(12) United States Patent
Tal et al.

(10) Patent No.: US 11,116,948 B2
(45) Date of Patent: Sep. 14, 2021

(54) DEVICES AND METHODS FOR IMAGING AND TREATING BLOOD VESSELS

(71) Applicant: A.V. MEDICAL TECHNOLOGIES, LTD, Tel-Aviv (IL)

(72) Inventors: Michael Gabriel Tal, Tel-Aviv (IL); Ilan Carmel, Tel-Mond (IL); Ronny Winshtein, Ramat-Hasharon (IL)

(73) Assignee: A.V. MEDICAL TECHNOLOGIES, LTD, Tel-Aviv (IL)

( * ) Notice: Subject to any disclaimer, the term of this patent is extended or adjusted under 35 U.S.C. 154(b) by 1118 days.

(21) Appl. No.: 15/110,587

(22) PCT Filed: Jan. 6, 2015

(86) PCT No.: PCT/IB2015/000010
§ 371 (c)(1),
(2) Date: Jul. 8, 2016

(87) PCT Pub. No.: WO2015/104631
PCT Pub. Date: Jul. 16, 2015

(65) Prior Publication Data
US 2016/0331944 A1 Nov. 17, 2016

Related U.S. Application Data

(60) Provisional application No. 61/924,886, filed on Jan. 8, 2014.

(51) Int. Cl.
*A61M 25/10* (2013.01)
*A61M 25/00* (2006.01)
(Continued)

(52) U.S. Cl.
CPC ........... *A61M 25/104* (2013.01); *A61B 6/504* (2013.01); *A61M 5/007* (2013.01);
(Continued)

(58) Field of Classification Search
CPC .............. A61M 25/104; A61M 25/003; A61M 25/007; A61M 5/007; A61M 2025/0079;
(Continued)

(56) References Cited

U.S. PATENT DOCUMENTS

| 4,585,000 A | 4/1986 | Hershenson |
| 4,794,928 A | 1/1989 | Kletschka |

(Continued)

FOREIGN PATENT DOCUMENTS

| CN | 201058169 | 5/2008 |
| EP | 0770405 A2 | 5/1997 |

(Continued)

OTHER PUBLICATIONS

Nayak, Keshav R., et al. "A novel technique for ultra-low contrast administration during angiography or intervention." Catheterization and Cardiovascular Interventions 75, No. 7 (2010): 1076-1083.*

(Continued)

*Primary Examiner* — Carolyn A Pehlke
(74) *Attorney, Agent, or Firm* — Carter, DeLuca & Farrell LLP

(57) ABSTRACT

Rapid exchange balloon catheter, and applications thereof. The balloon catheter includes a shaft and a guidewire channel. Shaft includes infusion and inflation walls. Infusion wall encloses an infusion lumen and comprises fluid inlet and fluid outlet located distally to fluid inlet. The inflation lumen extending axially therealong opened at a distal end thereof into an inner volume of a dilatation balloon. Guidewire channel is sized to closely fit over a pre-scribed guidewire for allowing unhindered passing therethrough with the guidewire. Guidewire channel includes a channel distal end protruding distally from the balloon with a distal guidewire opening, and a channel proximal end with a proximal guidewire opening at the shaft between fluid inlet (Continued)

and fluid outlet. Applications include methods for angioplasty and revascularization in which a single balloon catheter is used for dilatation and/or occlusion, and for delivering fluid proximally to the balloon.

21 Claims, 14 Drawing Sheets

(51) Int. Cl.
  *A61B 6/00*        (2006.01)
  *A61M 5/00*        (2006.01)
  *A61M 25/01*       (2006.01)

(52) U.S. Cl.
  CPC ......... *A61M 25/003* (2013.01); *A61M 25/007* (2013.01); *A61M 2025/0079* (2013.01); *A61M 2025/0183* (2013.01); *A61M 2025/105* (2013.01); *A61M 2202/0474* (2013.01)

(58) Field of Classification Search
  CPC .... A61M 2025/0183; A61M 2025/105; A61M 2025/1056; A61M 2202/0474; A61M 25/0015; A61B 6/504
  See application file for complete search history.

(56) References Cited

U.S. PATENT DOCUMENTS

| | | |
|---|---|---|
| 5,069,673 A | 12/1991 | Shwab |
| 5,250,038 A | 10/1993 | Melker et al. |
| 5,267,979 A | 12/1993 | Appling et al. |
| 5,306,247 A | 4/1994 | Pfenninger |
| 5,318,032 A | 6/1994 | Lonsbury et al. |
| 5,344,402 A | 9/1994 | Crocker |
| 5,368,567 A | 11/1994 | Lee |
| 5,439,447 A | 8/1995 | Miraki |
| 5,523,092 A | 6/1996 | Hanson et al. |
| 5,693,088 A | 12/1997 | Lazarus |
| 5,836,967 A | 11/1998 | Schneider |
| 5,908,407 A | 6/1999 | Frazee et al. |
| 6,010,521 A | 1/2000 | Lee et al. |
| 6,017,323 A | 1/2000 | Chee |
| 6,022,336 A | 2/2000 | Zadno-Azizi et al. |
| 6,051,020 A | 4/2000 | Goicoechea et al. |
| 6,231,543 B1 | 5/2001 | Hegde et al. |
| 6,440,097 B1 | 8/2002 | Kupiecki |
| 6,485,500 B1 | 11/2002 | Kokish et al. |
| 6,544,217 B1 | 4/2003 | Gulachenski |
| 6,663,648 B1 | 12/2003 | Trotta |
| 7,182,755 B2 | 2/2007 | Tal |
| 7,195,611 B1 | 3/2007 | Simpson et al. |
| 7,873,404 B1 † | 1/2011 | Patton |
| 8,241,248 B2 | 8/2012 | Kassab |
| 8,532,749 B1 † | 9/2013 | Patton |
| 9,248,263 B2 | 2/2016 | Sarradon |
| 2002/0143251 A1 | 10/2002 | Richardson et al. |
| 2003/0204236 A1 | 10/2003 | Letort |
| 2004/0068250 A1 | 4/2004 | Boutilette et al. |
| 2004/0116832 A1 | 6/2004 | Friedrich et al. |
| 2004/0122465 A1 | 6/2004 | McMurtry et al. |
| 2006/0064058 A1 | 3/2006 | Coyle |
| 2006/0253071 A1 | 11/2006 | Zattera |
| 2007/0060882 A1 | 3/2007 | Tal |
| 2007/0129752 A1 | 6/2007 | Webler et al. |
| 2008/0091140 A1* | 4/2008 | Hamburger ......... A61M 25/007 604/93.01 |
| 2008/0221550 A1 | 9/2008 | Lee |
| 2009/0312827 A1 | 12/2009 | Stapleton |
| 2010/0198186 A1 | 8/2010 | Ackermann |
| 2010/0256506 A1 | 10/2010 | Mohl |
| 2011/0270373 A1 | 11/2011 | Sampognaro et al. |
| 2012/0265135 A1 | 10/2012 | Porter |
| 2012/0265287 A1 | 10/2012 | Sharma et al. |
| 2013/0172661 A1 | 7/2013 | Farnan et al. |
| 2013/0345628 A1* | 12/2013 | Berger ................ A61M 25/003 604/101.05 |
| 2014/0142598 A1* | 5/2014 | Fulton, III ..... A61B 17/320725 606/159 |
| 2014/0316263 A1 † | 10/2014 | Murphy |
| 2015/0209557 A1 | 7/2015 | Tal et al. |

FOREIGN PATENT DOCUMENTS

| | | |
|---|---|---|
| WO | 94/02196 A1 | 2/1994 |
| WO | 9505862 A1 | 3/1995 |
| WO | 99/42059 A2 | 8/1999 |
| WO | 01/56645 A1 | 8/2001 |
| WO | 2012/110598 A1 | 8/2012 |
| WO | 2014/009809 A1 | 1/2014 |
| WO | 2014/113257 A2 | 7/2014 |

OTHER PUBLICATIONS

Dec. 12, 2013 International Search Report issued in International Patent Application No. PCT/IB2013/001895.
Jul. 30, 2014 International Search Report issued in International Patent Application No. PCT/US2014/010752.
Apr. 22, 2015 International Search Report issued in International Patent Application No. PCT/IB2015/000010.
Oct. 13, 2016 International Search Report issued in International Patent Application No. PCT/IB2016/053804.
Besarab et al "Catheter Management in Hemodialysis Patients: Delivering Adequate Flow". Clinical Journal of the American Society of Nephrology. vol. 6 (2011): 227-234.
Hacker et al "Fibrin Sheath Angioplasty: A Technique to Prevent Superior Vena Cava Stenosis Secondary to Dialysis Catheters". The International Journal of Angiology: Official Publication of the International College of Angiology, Inc. 21-3 (2012): 129-134.
Rejection Decision dated Dec. 31, 2019 issued in corresponding CN Appln. No. 201580003906.1.

\* cited by examiner
† cited by third party

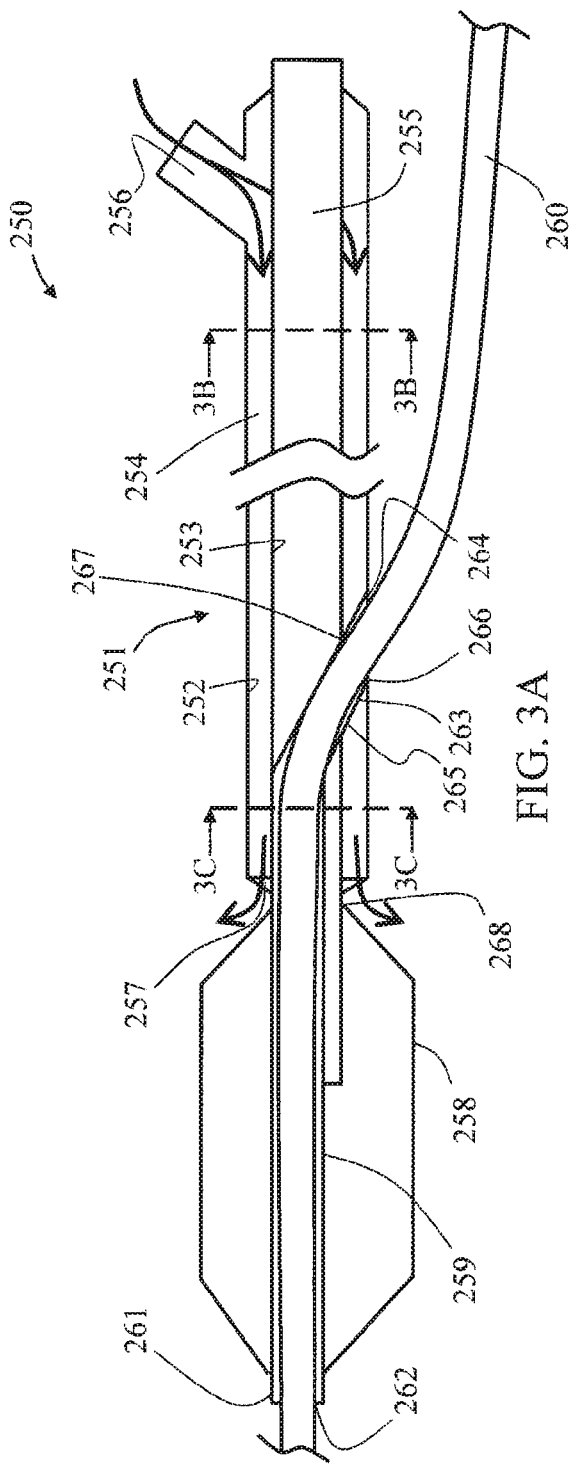
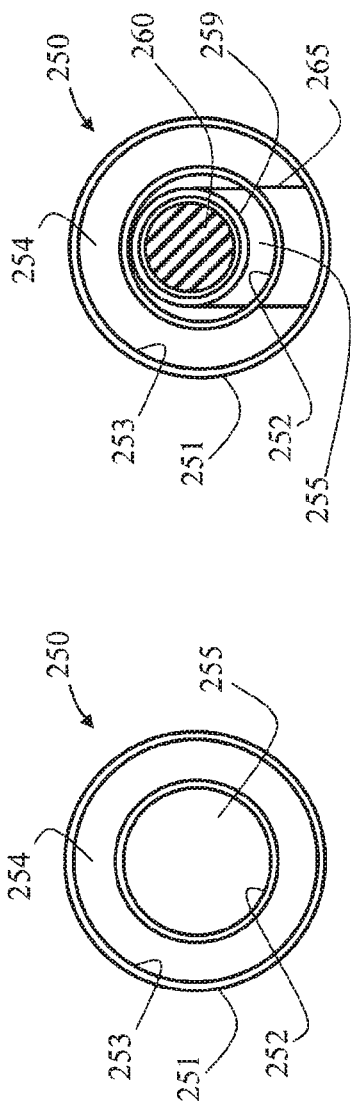
FIG. 3A
FIG. 3B
FIG. 3C

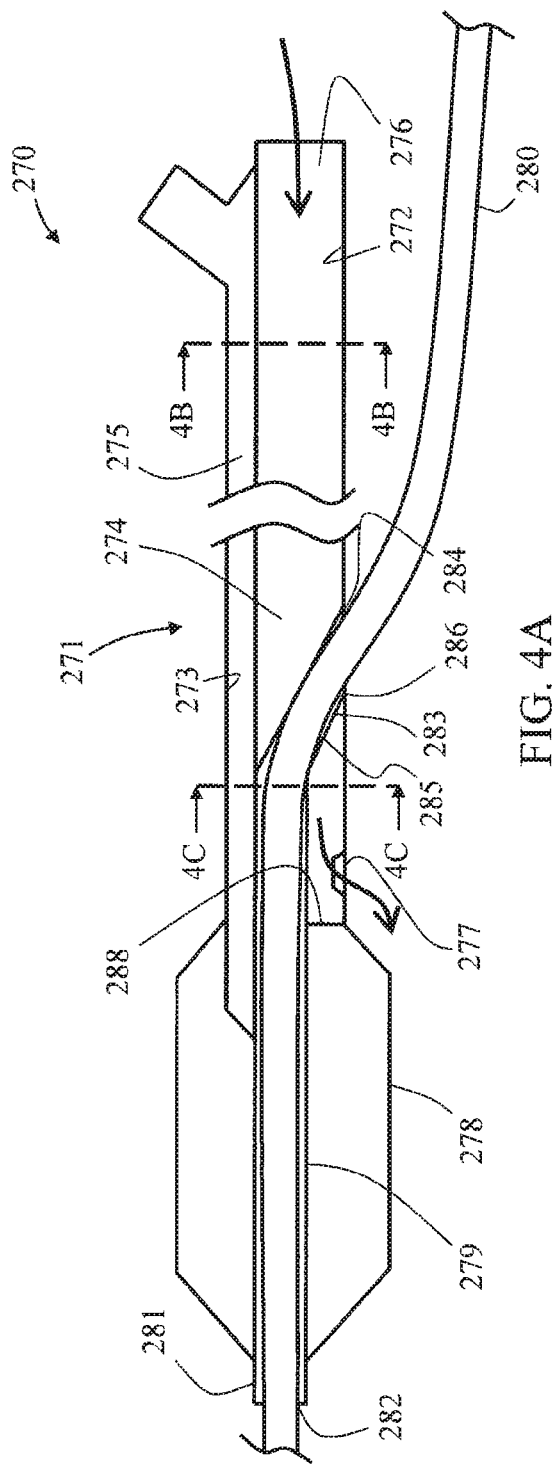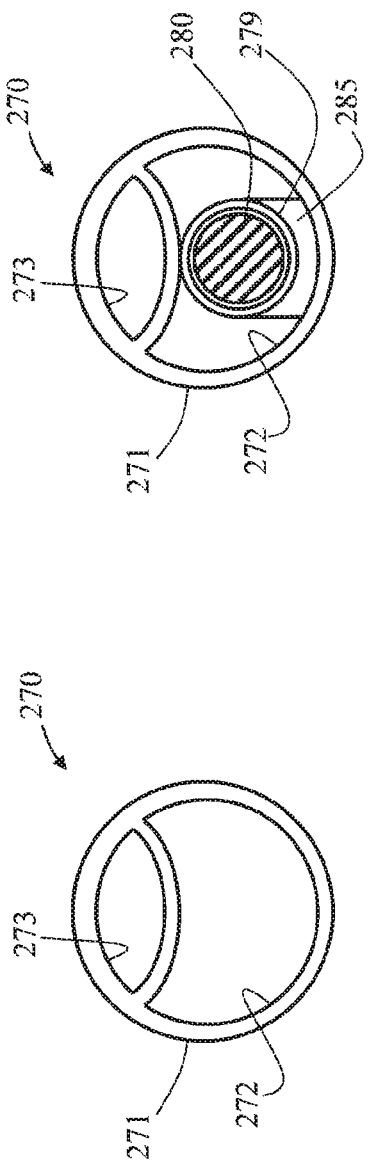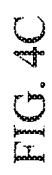
FIG. 4A
FIG. 4B
FIG. 4C

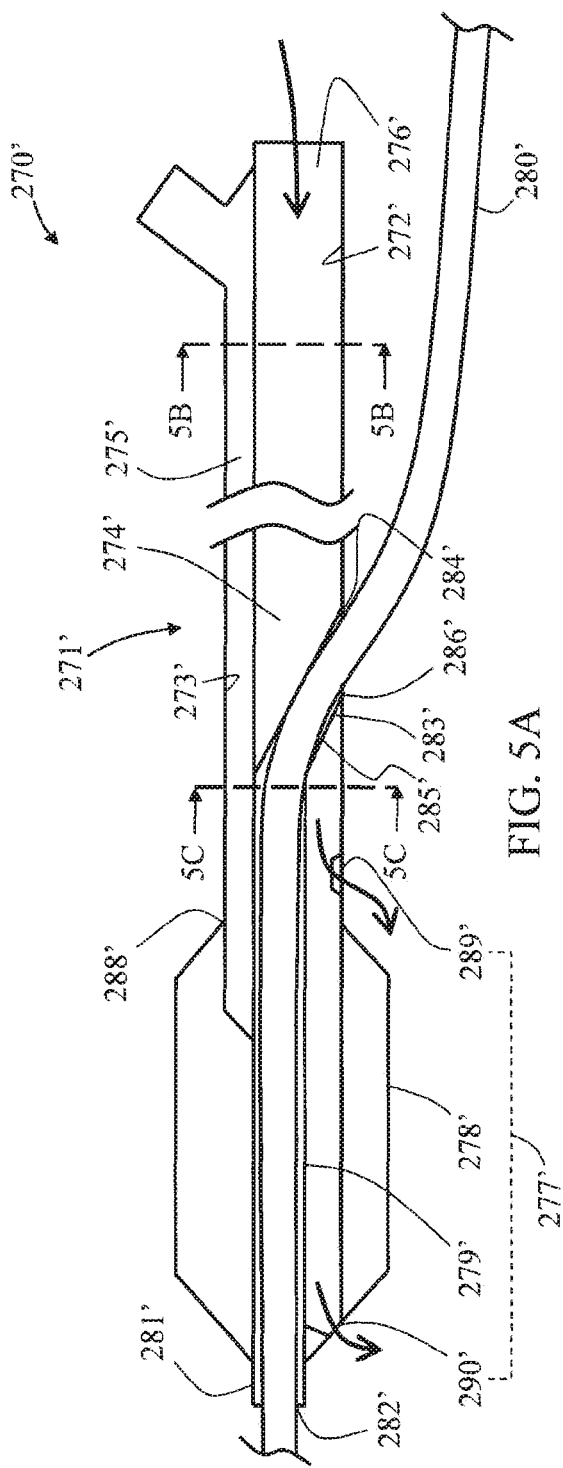
FIG. 5A
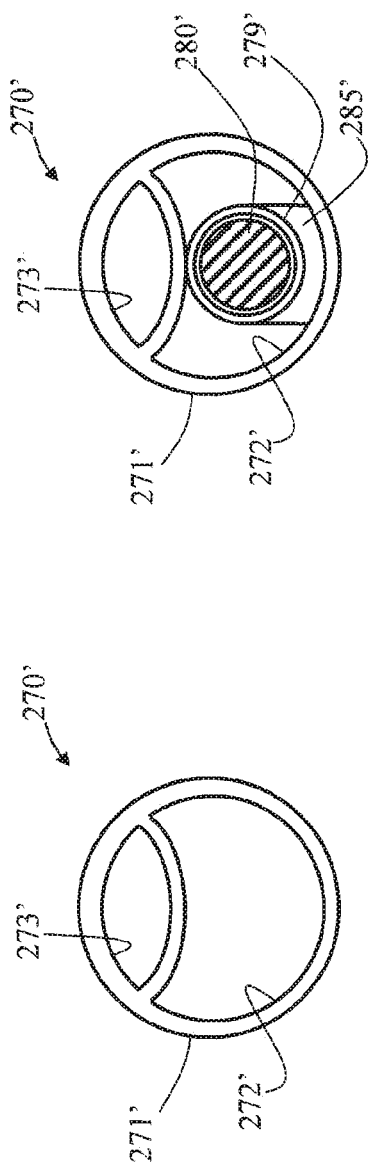
FIG. 5B
FIG. 5C

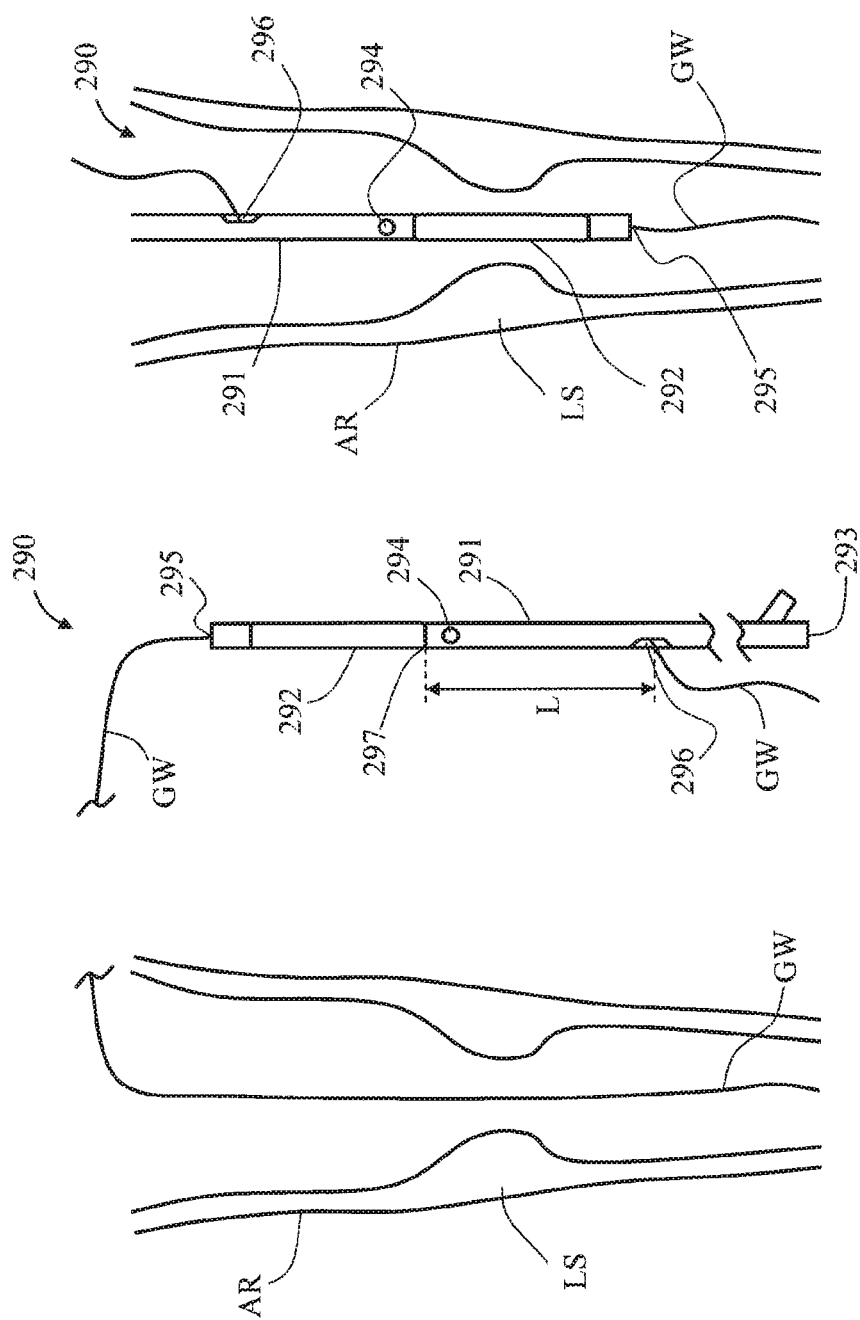

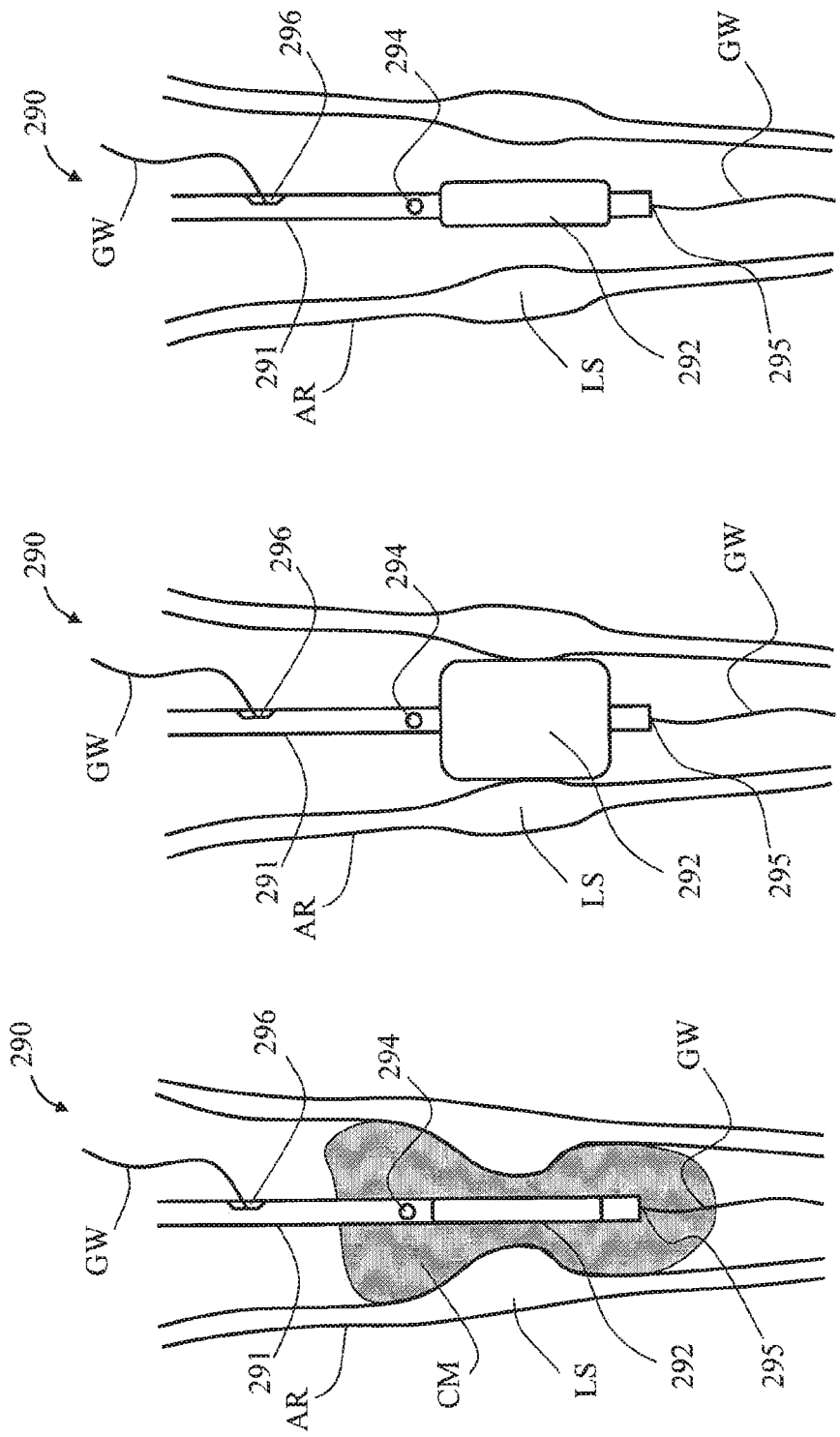

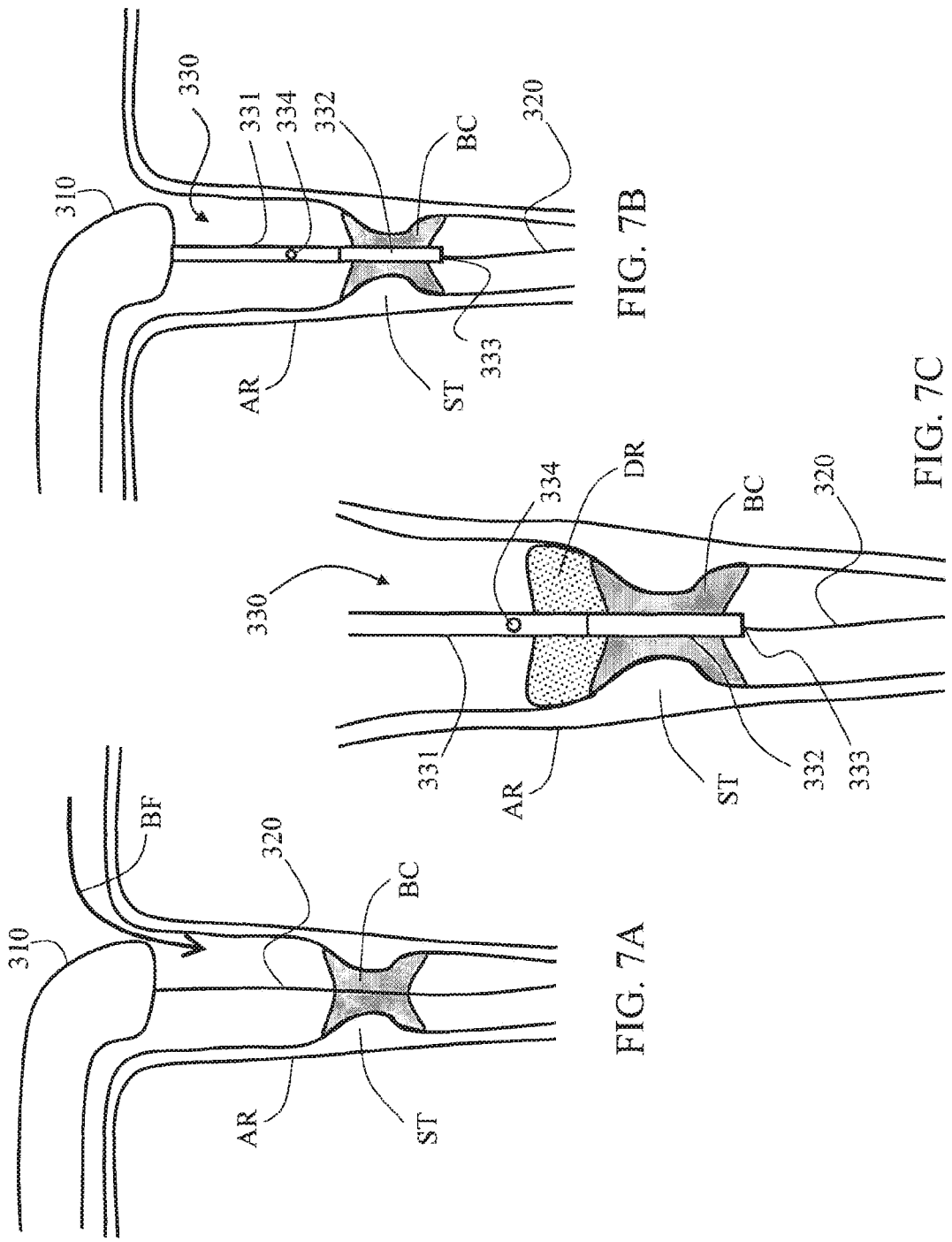

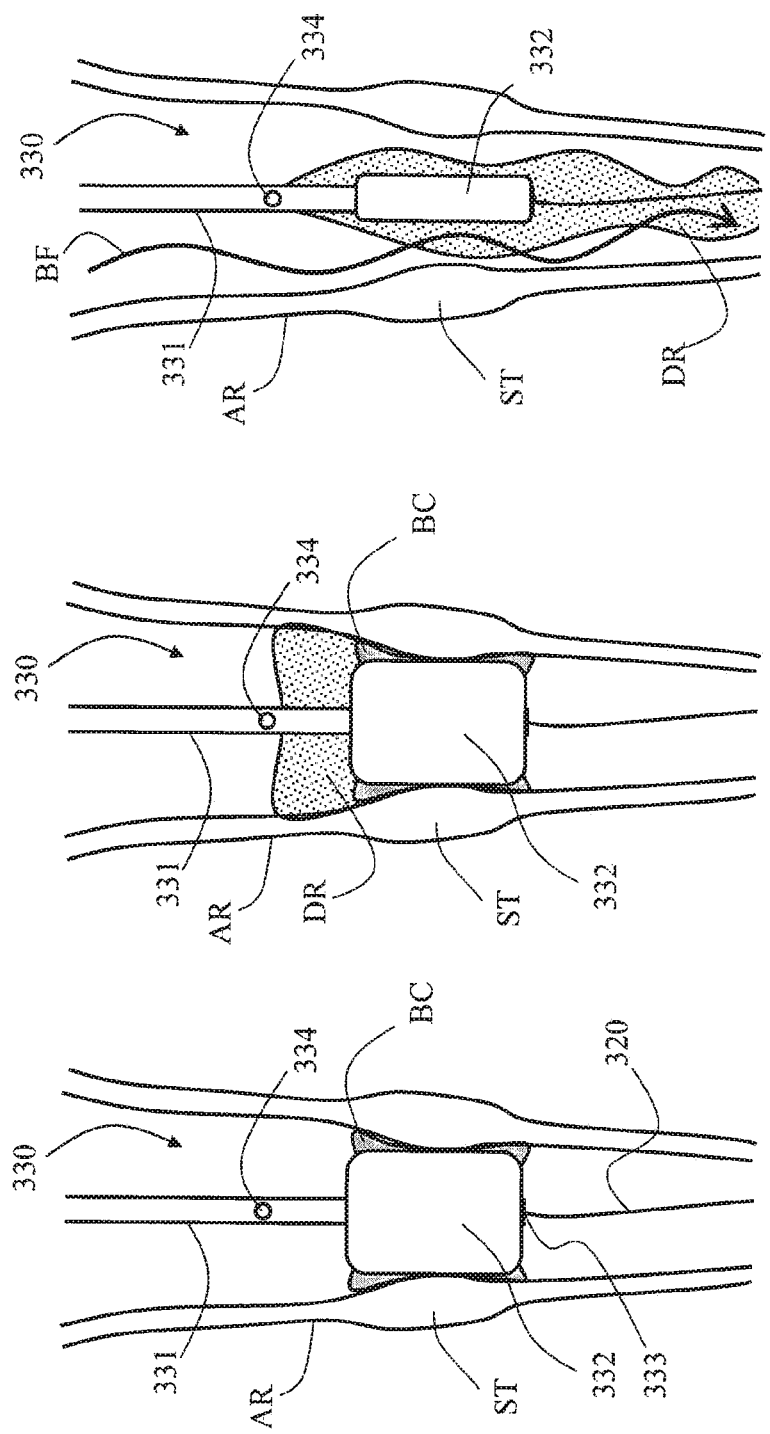

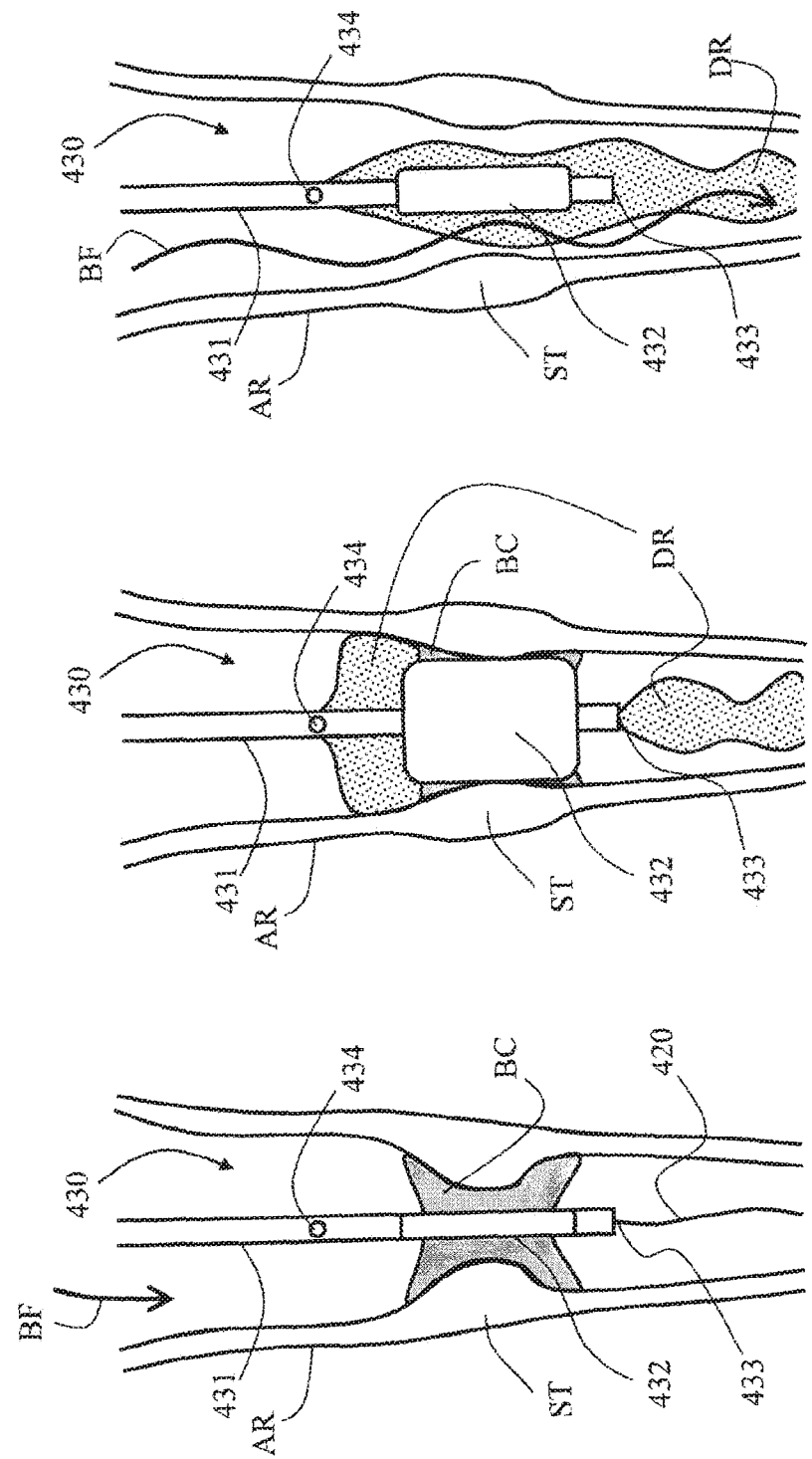

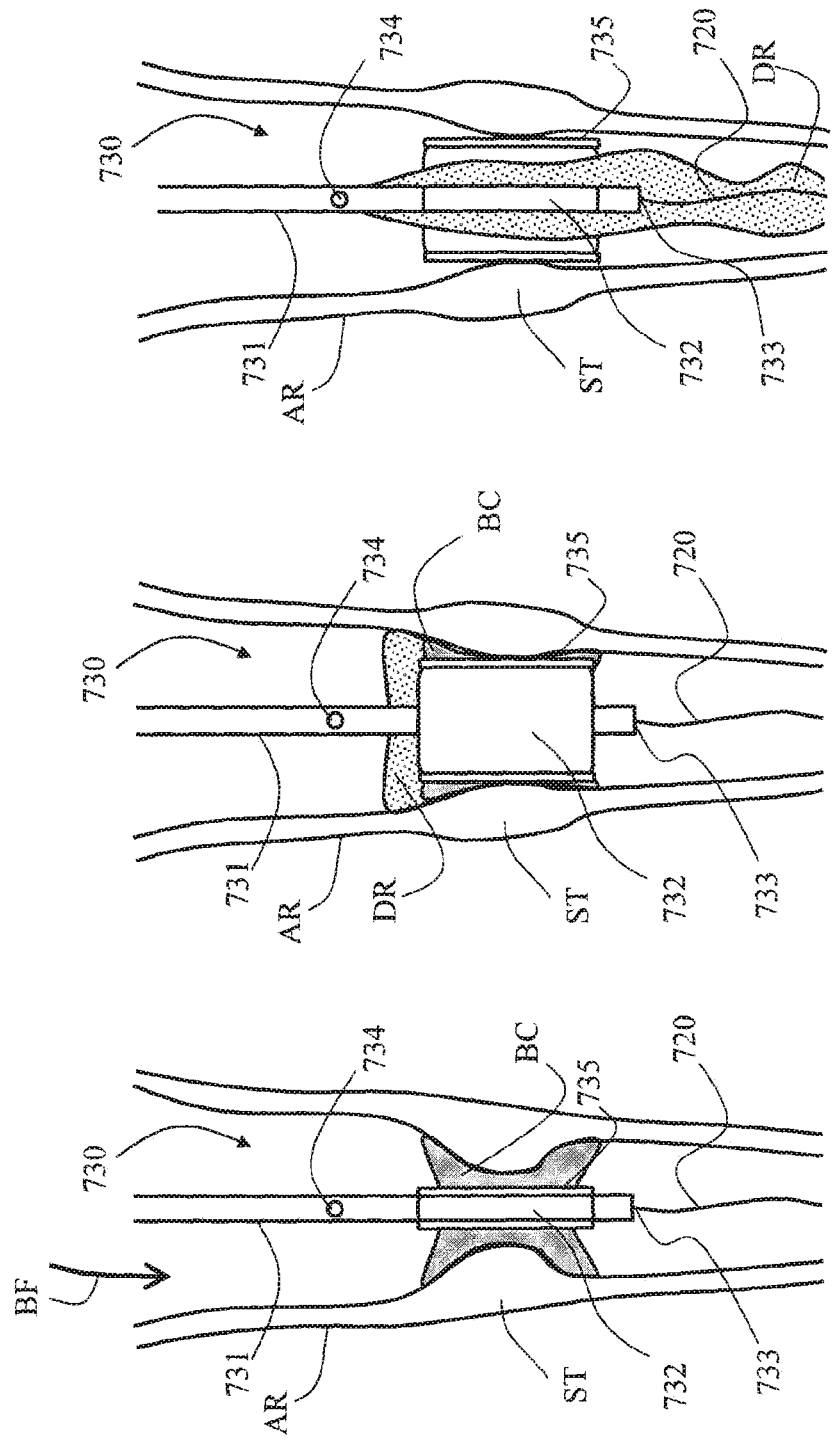

DEVICES AND METHODS FOR IMAGING AND TREATING BLOOD VESSELS

RELATED APPLICATIONS

This application is a U.S. National Stage Entry Under 35 U.S.C. 371 of International Application No. PCT/IB2015/000010 filed Jan. 6, 2015, which claims the benefit of priority under 35 U.S.C. § 119(e) from U.S. Provisional Patent Application No. 61/924,886 filed on Jan. 8, 2014, the disclosures of which are incorporated herein by reference in their entireties.

FIELD AND BACKGROUND OF THE INVENTION

The present invention, in some embodiments thereof, relates to medical devices and methods, and in particular to balloon catheters and applications thereof for imaging and treating blood vessels.

Problems associated with current angioplasty and revascularization procedures commonly include: use of multiple catheters and multiple device exchanges, each associated with additional radiation to visualize position of each catheter; rapid blood flow in the access area limits visualization of blood vessels and requires repeated contrast injections and angiograms; and/or risk of clot migration to artery when performing de-clotting procedures.

The angioplasty procedure as currently practiced often requires use of more than one catheter. Placement of a standard angioplasty catheter over a guidewire requires that a length of wire protrude outside the patient that is longer than the catheter itself. This allows the operator to always be able to maintain contact with the external guidewire while advancing the balloon into the patient, to be able to maintain the distal guidewire across the lesion of interest and to maintain a grip on the guidewire during catheter removal. Having to reinsert a guidewire takes extra time and increases the risk of the procedure. The length of wire required to perform this procedure can include as much as 150 to 200 cm protruding from a patient. This length must be kept sterile throughout the procedure and usually requires a second person in sterile scrub to hold it and maintain it within the sterile field.

Catheterization systems, such as those involving rapid exchange (RX) catheters, have been designed that allow advancement or removal of an angioplasty catheter over a guidewire by a single operator while not losing the ability to hold the guidewire. Use of a rapid exchange catheterization system reduces guidewire length, decreases the risk of a break in sterility, and obviates the need for an assistant during the procedure. Additionally, having to advance a conventional catheter along the entire length of a guidewire imposes significant friction, taxing the operator's ability to push the catheter. This friction also detracts from the physician's sense of tactile response which is important to the success of the procedure.

In several instances, when there is a need to combine drug infusion and angioplasty using a rapid exchange (RX) balloon catheter, the procedure is more difficult and may necessitate removal of the balloon catheter and exchanging it with a different catheter for injecting the medication, and then replacing the balloon over the wire if needed.

Cerebral vasospasm is a serious complication of intra cranial bleeding, especially sub arachnoid hemorrhage. What is seen in these patients is a narrowing, sometimes focal, of the cerebral blood vessels. This vasospasm causes ischemic injury and sometimes irreversible brain damage. Treatment of vasospasm is based on a combination of standard angioplasty and local infusion of medications to allow and promote vasodilatation.

Coronary artery disease (CAD) is a most common type of heart disease and cause of heart attacks. It is caused by plaque building up along the inner walls of the arteries of the heart, which narrows the arteries and reduces blood flow to the heart, possibly causing ischemia of the myocardial cells. A "heart attack" (myocardial infarction) occurs at death of myocardial cells due to prolonged ischemia. Reperfusion therapy is performed to restore blood flow through blocked arteries, commonly including one of: administration of thrombolytic drugs ("thrombolysis"), coronary angioplasty also known as percuraneous coronary intervention ("PCI") and coronary artery bypass surgery ("CABG").

Thrombolysis is used to break up and dissolve blood clots by stimulating secondary fibrinolysis by plasmin through infusion of analogs of tissue plasminogen activator (tPA). Effectiveness of thrombolytic therapy is highest in the first two hours since irreversible injury occurs within 2-4 hours of the infarction. After 12 hours the risk associated with thrombolytic therapy outweighs any benefit. In cases of failure of the thrombolytic agent to open the infarct-related coronary artery, the patient is then either treated conservatively with anticoagulants or with performing rescue PCI. Complications, particularly bleeding, are significantly higher with rescue PCI than with primary PCI due to the action of the thrombolytic agent.

Percutaneous coronary intervention (PCI) is a non-surgical procedure used to treat the stenotic (narrowed) coronary arteries of the heart, commonly including the following steps:

(i) creating a percutaneous access usually into the femoral artery using an introducer needle and placing a sheath introducer in the opening.
(ii) introducing a guiding catheter through the introducer sheath and pushing it forward until reaching the entry of the coronary artery. Injecting contrast enhancing medium via a distal opening at the guiding catheter and using real time X-ray visualization to assess condition and target ill location.
(iii) inserting a guidewire through the guiding catheter and into the coronary artery, passing across the blockage.
(iv) delivering a dilatation balloon catheter over the guidewire so that the deflated balloon will be inside of the blockage.
(v) inflating the balloon to compress the atheromatous plaque and stretches the artery wall to expand.
(vi) in case a stent is delivered with the balloon catheter, the balloon inflation causes the stent to open and deploy to support the new stretched open position of the artery from the inside.

Aortic valve stenosis (AS) is a disease of the heart valves in which the opening of the aortic valve is narrowed. In adults, symptomatic severe aortic stenosis usually requires aortic valve replacement (AVR). AVR approaches include open heart surgery, minimally invasive cardiac surgery (MICS) and minimally invasive catheter-based (percutaneous) aortic valve replacement.

In view of the current state of the art, along with associated limitations thereof, there is need for developing new and improved techniques (devices, methods) for imaging and treating blood vessels.

SUMMARY OF THE INVENTION

The present invention, in some embodiments thereof, relates to medical devices and methods, and in particular to balloon catheters and applications thereof for imaging and treating blood vessels.

In an aspect of some embodiments according to the present disclosure, there is provided a method for revascularizing a blood vessel, which comprises at least one of the following steps (not necessarily in same order):

locating a target portion in the blood vessel filled with an obstruction.

providing a dilatation catheter comprising an elongated tubular wall enclosing an infusion lumen extending between a proximal end and a distal end thereof, an expandable member located at the distal end, and a first fluid exit at the wall in fluid communication with the lumen.

positioning the dilatation catheter in the blood vessel such that the expandable member is in apposition to the target portion and the first fluid exit is toward the obstruction relative to blood flow direction in the blood vessel.

expanding the expandable member to dilate the blood vessel about the target portion.

applying an occlusion member to occlude the blood vessel below the first fluid exit.

injecting an obstruction treatment fluid through the infusion lumen via the first fluid exit until a chosen amount is accumulated above the obstruction.

allowing the obstruction to soak in the accumulated amount for a chosen period.

collapsing the expandable member.

In some embodiments, the target portion has vascular stenosis and/or the obstruction includes thrombus or embolus (e.g., including blood clots).

In some embodiments, the obstruction treatment fluid includes a thrombolytic agent. Optionally, the injecting occurs before, during and/or after the expanding of the expandable member. Optionally, the accumulated amount is at least 1 cc.

In some embodiments, the method includes a step of imaging the blood vessel prior to the locating of the target portion.

In some embodiments, the method includes a step of delivering a contrast enhancing medium adjacent the obstruction between the expandable member and the first fluid exit. Optionally, the contrast enhancing medium is delivered through the infusion lumen and the first fluid exit. Optionally, the infusion lumen is flushed with a cleaning medium between the injecting of the obstruction treatment fluid and the delivering of the contrast enhancing medium. Optionally and alternatively, the contrast enhancing medium is delivered through a second lumen sealed to the infusion lumen. Optionally, the delivering occurs continuously or repeatedly before, during and/or after the expanding of the expandable member, or optionally, before, during and/or after the collapsing thereof.

In some embodiments, the first fluid exit is proximal to the expandable member. Optionally, the first fluid exit is distal to the expandable member.

In some embodiments, the occlusion member is the expandable member or portion thereof and wherein the applying of the occlusion member is included in the expanding of the expandable member. The occlusion member may be a compliant balloon or a noncompliant balloon.

In some embodiments, the method includes a step of inserting a guidewire into the blood vessel across the target portion, wherein the positioning of the dilatation catheter includes passing the dilatation catheter over the guidewire. Optionally, the guidewire is passed through the infusion lumen and a guidewire opening at the dilatation catheter distal end. Optionally, the guidewire is withdrawn from the guidewire opening or from the infusion lumen after the positioning of the dilatation catheter. Optionally, the withdrawing of the guidewire facilitates blood perfusion between the first fluid exit and the guidewire opening.

In some embodiments, the dilatation catheter includes a second fluid exit in direct communication with the infusion lumen distal to the expandable member. Optionally, the second fluid exit is a guidewire exit. Optionally, the injecting of the obstruction treatment fluid causes it to exit through the second fluid exit.

In some embodiments, the dilatation catheter comprising a plurality of adjacent fluid exits comprising the first fluid exit. Optionally, the plurality of fluid exits is arranged radially and/or longitudinally. In some embodiments, the first fluid exit includes an opening and/or normally closed lips.

In some embodiments, the dilatation catheter includes at its distal end a plurality of openings in direct communication with the infusion lumen, which comprises at least one distal opening distal to the expandable member and at least one proximal opening proximal to the expandable member. Optionally, the plurality of openings are configured such that a ratio between a first exit flow rate, through the at least one distal opening, and a second exit flow rate, through the at least one proximal opening, can be regulated or met in relation to a known pressure gradient therebetween. Optionally, the plurality of openings are configured such that the total cross section of the at least one distal opening is smaller than the total cross section of the at least one proximal opening by a known derivative. Optionally, the known derivative is equal or greater than 2, optionally equal or greater than 5, optionally equal or greater than 10, or higher, or lower, or an intermediate value. Optionally, the regulation is determined by guidewire positioning in the infusion lumen.

In an aspect of some embodiments of the present disclosure, there is provided also a method for treating an aortic stenosis, which comprises at least one of the following steps (not necessarily in same order):

inserting a guide wire through an aorta into a left ventricle.

providing a dilatation catheter comprising an elongated tubular wall enclosing an infusion lumen extending between a proximal end and a distal end thereof, an expandable member located at the distal end, and a fluid exit at the wall in fluid communication with the lumen, wherein the expandable member is provided contracted.

passing the dilatation catheter over the guidewire such that the expandable member is in apposition to a native aortic valve.

expanding the expandable member to dilate the native aortic valve.

applying an occlusion member to occlude the entrance to the native aortic valve.

injecting a fluid through the infusion lumen via the fluid exit.

contracting the expandable member.

In some embodiments, the expandable member is provided enclosed with a collapsed expandable valve prosthesis. Optionally, the expandable valve prosthesis is self-expandable or it may be balloon-expandable.

In some embodiments, the fluid includes a medicament.

In some embodiments, the injecting of the fluid occurs before, during and/or after the expanding.

In some embodiments, the method includes the step of delivering a contrast enhancing medium adjacent the natural aortic valve between the expandable member and the fluid exit. Optionally, the contrast enhancing medium is delivered through the infusion lumen and the fluid exit. Optionally, the infusion lumen is flushed with saline between the injecting and the delivering. Optionally and alternatively, the contrast enhancing medium is delivered through a second lumen sealed to the infusion lumen. Optionally, the delivering of the contrast enhancing medium occurs continuously or repeatedly before, during and/or after the expanding of the expandable member and/or before, during and/or after the contracting thereof.

In some embodiments, the fluid exit is proximal or optionally distal to the expandable member.

In some embodiments, the occlusion member is the expandable member or portion thereof and wherein the applying is included in the expanding. The occlusion member may be a compliant balloon or a noncompliant balloon.

In some embodiments, the guidewire is passed through the infusion lumen and a guidewire opening at the dilatation catheter distal end. Optionally, the guidewire is withdrawn from the guidewire opening or from the infusion lumen after the passing of the dilatation catheter. Optionally, the withdrawing of the guidewire facilitates blood perfusion between the guidewire opening and the fluid exit. Optionally, fluid injecting causes the fluid to exit through the guidewire opening.

In some embodiments, the expandable member is repeatedly expanded and contracted in a timely manner for allowing blood flowing from the left ventricle to the aorta in between medicament injection and/or contrast enhancing medium delivery.

In an aspect of some embodiments according to the present disclosure, there is provided a rapid exchange balloon catheter which comprises a shaft and a guidewire channel. In some embodiments, the shaft comprises an infusion wall and an inflation wall. In some embodiments, the infusion wall encloses an infusion lumen extending axially therealong. In some embodiments, the infusion wall also comprises a fluid inlet and a fluid outlet located distally to the fluid inlet.

In some embodiments, the inflation wall encloses an inflation lumen extending axially therealong opened at a distal end thereof into an inner volume of a dilatation balloon.

In some embodiments, the guidewire channel is sized to closely fit, snugly, over a prescribed guidewire for allowing unhindered passing therethrough with the prescribed guidewire. In some embodiments, the guidewire channel comprises a channel distal end protruding distally from the balloon with a distal guidewire opening, and a channel proximal end with a proximal guidewire opening at the shaft between the fluid inlet and the fluid outlet. The guidewire channel may be sealed or unsealed to the infusion lumen and to the inflation lumen.

In some embodiments, the guidewire channel includes an inclined portion configured to skew the prescribed guidewire upon forcing thereof through the inclined portion. Optionally, the inclined portion is curved towards the infusion wall, and the proximal guidewire opening is provided through a hole at the infusion wall. Optionally, alternatively or additionally, the inclined portion is curved towards the inflation wall, and the proximal guidewire opening is provided through a hole at the inflation wall. Optionally, the guidewire channel includes a tubular portion.

In some embodiments, the proximal guidewire opening is distanced 10 cm to 30 cm from proximal boundary of the balloon. Optionally, the distance between the distal guidewire opening and the proximal guidewire opening is 10 cm to 50 cm, optionally 20 cm to 30 cm, or higher, or lower, or an intermediate value.

In some embodiments, the fluid outlet includes at least one opening located proximally to the balloon. Optionally, the at least one opening is distanced 1 cm or less from proximal boundary of the balloon. Optionally, alternatively or additionally, the fluid outlet includes at least one opening located distally to the balloon.

In some embodiments, least one of the infusion wall and the inflation wall is segmented and includes segments of different forms and/or rigidity. Optionally, the infusion lumen includes a rigid segment proximally to the proximal guidewire opening, and an underlapping portion of the inflation wall is flexible and/or elastic. Optionally, the infusion lumen includes a flexible segment proximally to the proximal guidewire opening, and an overlapping portion of the inflation wall is rigid. Optionally, at least one of the segments includes a hypotube.

In an aspect of some embodiments of the present disclosure there is also provided a method, which comprises at least one of the following steps (not necessarily in same order):

inserting a guidewire in a blood vessel having a lesion such that the guidewire is provided across the lesion.

providing a balloon catheter comprising a dilatation balloon, a fluid inlet, a fluid outlet adjacent the dilatation balloon, a distal guidewire opening, and a proximal guide opening located between the fluid outlet and the fluid inlet and distanced 30 cm or less from a proximal boundary of the dilatation balloon.

passing the guidewire through the distal guidewire opening and the proximal guidewire opening and pushing the balloon catheter in the blood vessel such that the fluid outlet is in approximation with the lesion.

injecting a contrast enhancing medium from the fluid outlet in a total amount equal or less than 2 cc, optionally equal or less than 1 cc, and producing an angiogram of the lesion.

delivering medicament to the lesion.

In some embodiments, the medicament is delivered from the fluid outlet. Optionally, the fluid inlet and/or fluid outlet is flushed with a cleaning medium between the injecting and the delivering. In some embodiments, the medicament includes a thrombolytic agent and/or a vasodilator agent such as nicardipine or nifedipine.

In some embodiments, the blood vessel is an obstructed coronary artery and/or a vasospatic cerebral blood vessel.

In some embodiments the method comprises the step of expanding the dilatation balloon to dilate the blood vessel about the lesion. Optionally, the expanding of the dilatation balloon is performed before the delivering of the medicament and/or before the injecting of the contrast enhancing medium. Optionally and alternatively, the expanding of the dilatation balloon is performed after the medicament delivering. Optionally, the injecting of the contrast enhancing medium is repeated after the medicament delivering and/or after the expanding of the dilatation balloon.

In some embodiments the method comprises the step of deflating the dilatation balloon. Optionally, the injecting of the contrast enhancing medium is repeated after the deflating. Optionally, the medicament delivering is performed after the deflating of the dilatation balloon, or optionally before deflating thereof.

In some embodiments, the dilatation balloon is provided enclosed with a collapsed expandable member such as a stent. Optionally, the expandable member may be self-expandable or balloon-expandable.

In some embodiments, the fluid outlet is located proximally to the dilatation balloon.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-3C schematically illustrate a first exemplary rapid exchange balloon catheter, in accordance with some embodiments of the present invention;

FIGS. 4A-4C schematically illustrate a second exemplary rapid exchange balloon catheter, in accordance with some embodiments of the present invention;

FIGS. 5A-5C schematically illustrate a third exemplary rapid exchange balloon catheter, in accordance with some embodiments of the present invention;

FIGS. 6A-6F schematically illustrate possible scenarios in a method for imaging and treating a blood vessel using an exemplary RX catheter, in accordance with some embodiments of the present invention;

FIGS. 7A-7F schematically illustrate possible scenarios in a method for revascularizing a blood vessel using a first exemplary dilatation catheter, in accordance with some embodiments of the present invention;

FIGS. 8A-8C schematically illustrate possible scenarios in a method for revascularizing a blood vessel using a second exemplary dilatation catheter, in accordance with some embodiments of the present invention;

FIGS. 11A-11C schematically illustrate possible scenarios in a method for revascularizing a blood vessel using a fifth exemplary dilatation catheter carrying a stent, in accordance with some embodiments of the present invention.

DESCRIPTION OF SPECIFIC EMBODIMENTS OF THE INVENTION

Figure 1A:
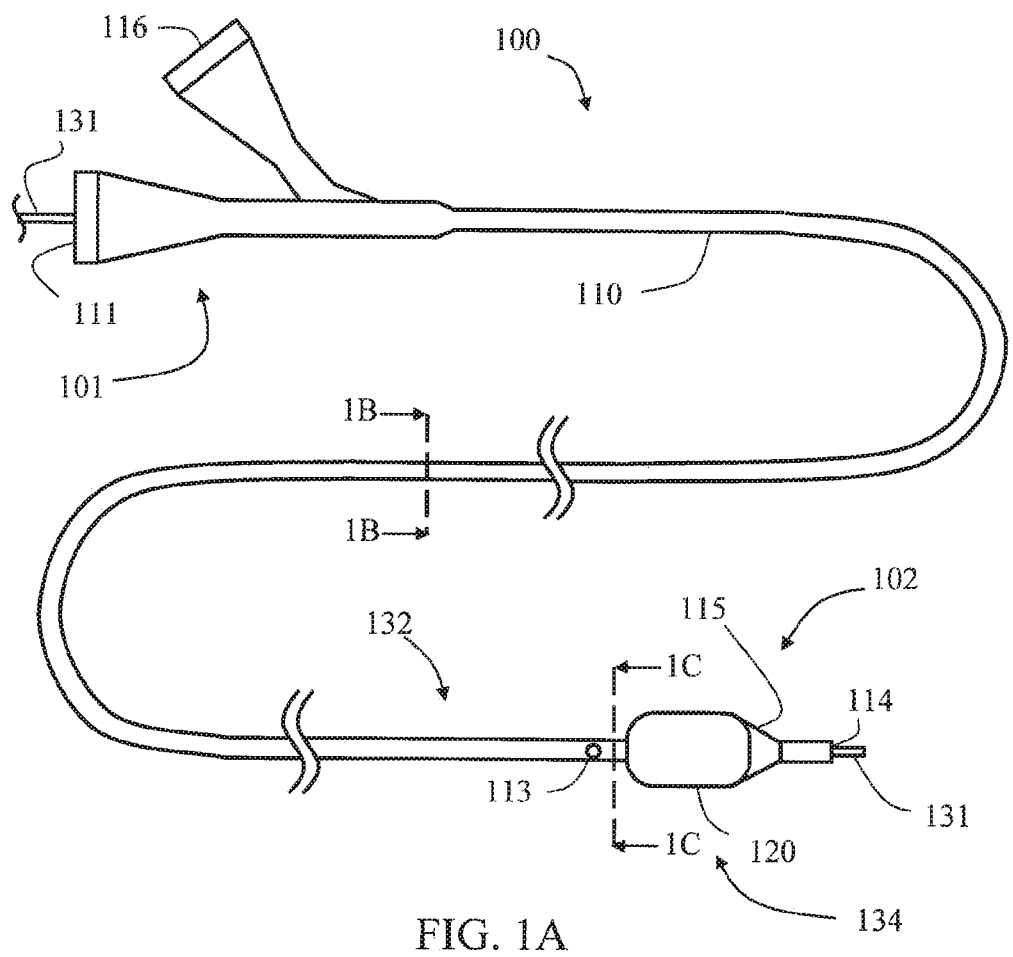
FIGS. 1A-1D schematically illustrate an exemplary balloon catheter comprising a combined infusion-guidewire lumen with selective valving mechanism, in accordance with some embodiments of the present invention.
Figure 1B:
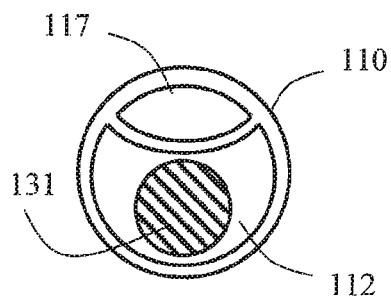
Figure 1C:
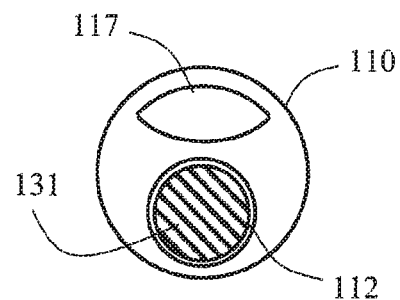
Figure 1D:
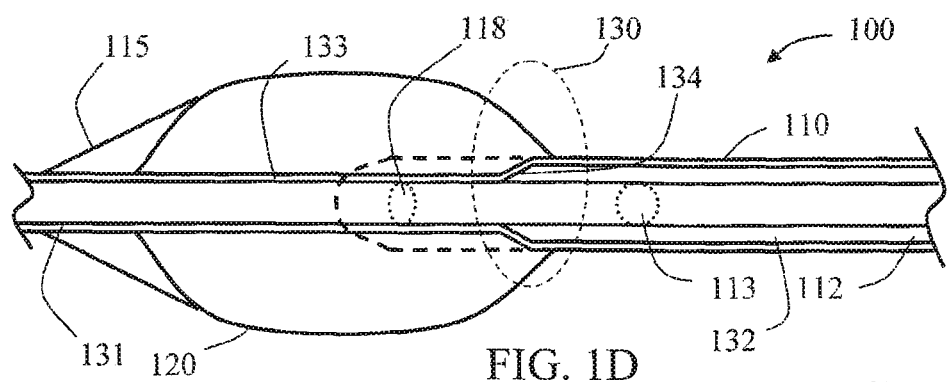

The present invention, in some embodiments thereof, relates to medical devices and methods, and in particular to balloon catheters and applications thereof for imaging and treating blood vessels.

The following exemplary embodiments are described in the context of exemplary balloon catheters for treating blood vessels. The invention is not limited only to the specifically described exemplary embodiments of devices and methods, and may also be adapted to various clinical applications without departing from the overall scope of the invention.

Exemplary Embodiments of Proximal Infusion Catheters

Referring to the drawings, FIGS. 1A-1D schematically illustrate an exemplary balloon catheter 100 comprising a combined infusion-guidewire lumen (referred to as infusion lumen 112) with a guidewire-based valving mechanism 130. Catheter 100 includes a shaft 110 having a length, a proximal end 101 and a distal end 102, and a wall enclosing infusion lumen 112 which is extending along shaft's 110 length and opened at both proximal end 101 and distal end 102 with corresponding proximal opening 111 and distal opening 114. Infusion lumen 112 is further opened with a lateral fluid outlet 113 (optionally comprising one or more openings) disposed in shaft's 110 wall between proximal end 101 and distal end 102.

An expandable member 120 is connected to shaft 110 at distal end 102, distal to lateral fluid outlet 113. An inflation lumen 117, sealed to infusion lumen 112, extends between a proximal inflation opening 116, at shaft's proximal end 101, and a distal inflation port 118, opened to an interior of expandable member 120. Expandable member 120 may be an inflatable balloon, optionally compliant, semi-compliant or non-compliant. Expandable member 120 may be bare, or drug coated, or mounted with a collapsed stent. Catheter distal end 102 may include or end with an optional beveled tip 115 for assisting in catheter delivery through narrowed, clotted and/or otherwise obstructed portions in the blood vessel. Beveled tip 115 may be an extension of expandable member 120 or it may be a separate member fixed to shaft 110. Beveled tip 115 may be elastic and/or hardened relatively to other parts or members of catheter 100.

A valving mechanism according to the present disclosure may be any type of controller, such as a mechanical device, for selectively controlling a flow parameter of a fluid, for example a flow rate. A valving mechanism may be set between two or more modes that inhibit fluid flow by different amounts. In some cases, the modes may include a fully closed mode in which flow is substantially absent, and a fully opened valve in which fluid is allowed to travel substantially unhindered by the valving mechanism. Intermediate flow restrictions are also possible. According to some exemplary embodiments of the present disclosure, a valving mechanism includes an elongated member such as a wire (e.g., a guide wire) operational to selectively pass through or withdraw from an infusion lumen portion sized and shaped substantially the same as external boundaries of a correlating portion thereof, being substantially narrowed as compared to a proximal portion of the infusion lumen located between a fluid inlet and a fluid outlet, such that when the wire occupies the narrowed infusion lumen portion then no flow or at least substantially no flow will pass therethrough. When the obstructing wire is fully withdrawn from the constricted or narrowed infusion lumen portion, fluid can pass therethrough. In an optional alternative embodiment, other valving means may be applied so that no fluid may pass through the narrowed infusion lumen portion also when the obstructing wire is absent, so that all or at least substantially all fluid will be delivered through a fluid outlet that is positioned proximal to the narrowed infusion lumen portion.

As shown in FIGS. 1A-1D, guidewire-based valving mechanism 130 may be provided in infusion lumen 112 distal to fluid outlet 113. Valving mechanism 130 is selectively operable to block distal opening 114 of infusion lumen 112 such that fluid passing distally through infusion lumen 112 shall exit mainly or solely through fluid outlet 113 rather than through distal opening 114. In case that valving mechanism 130 is set not to block distal opening 114, flow may pass via distal opening 114 at all or in a greater rate.

As shown, infusion lumen 112 defines a first segment 132, extending between proximal opening 111 and a boundary 134 (shown adjacent to fluid outlet 113 although it may be further distal), and a second segment 133, extending between boundary 134 and distal opening 114. In some embodiments, in first segment 132, infusion lumen 112 has a first minimal cross section area, and in second segment 133, infusion lumen 112 has a second minimal cross section area smaller than the first minimal cross section than in first segment 132. Valving mechanism 130 includes an elongated member, for example, a guide wire 131 selectively disposable in infusion lumen 112 at first segment 132 and/or second segment 133. Guide wire 131 is sized and configured to pass through proximal opening 111, infusion lumen 112 and distal opening 114, and therefore allow an over-the-wire delivery of catheter 100 thereupon.

In some embodiments, the second minimal cross sections is sized and shaped such that guide wire 131 can be selectively closely fit, snugly, in the second minimal cross section in order to achieve blocking of distal opening 114 and/or second segment 133 distal to fluid outlet 113. In some embodiments, the second minimal cross section is circular whereas the first minimal cross section is sized and shaped to virtually enclose a circle with identical dimensions to said second minimal cross section (as shown in the shape difference of infusion lumen 112 in FIG. 1B vs. FIG. 1C). The first minimal cross section may be of any shape such as circular, elliptic or crescent.

In an aspect of some embodiments, a method is disclosed for operating a balloon catheter, such as balloon catheter 100, according to the present disclosure, comprising at least one of the following steps (not necessarily in same order):

inserting guidewire 131 in a luminal vessel, such as a vein or an artery, optionally a coronary, a peripheral or dialysis target vessel.

delivering balloon catheter 100 in the luminal vessel over guidewire 131 to a chosen target.

inflating expandable member 120 to occlude, at least partially, the luminal vessel at the target.

infusing a fluid (e.g., a liquid or suspended medicament or contrast enhancing medium) through fluid outlet 113 such that minimal or no fluid passes beyond expandable member 120.

In some embodiments, the steps of inflating expandable member 120 and infusing a fluid are performed simultaneously and/or in overlap. In some embodiments, guide wire 131 is selectively occupying or withdrawn from second segment 133 in infusion lumen 112 according to need. In some embodiments, catheter 100 first engages guide wire 131 by inserting it via distal opening 114, or alternatively, by inserting guide wire 131 in infusion lumen 112 via proximal opening 111. In some embodiments, the infusing occurs while the expandable member is filled and/or expanded, optionally fully or partially. Optionally, the expandable member is contracted (e.g., deflated) after the infusing. In some embodiments, the expansion generates a dilatation force in a magnitude above a mechanical yield point of a stenotic blood vessel wall. Optionally, alternatively or additionally, the mechanical interaction between the filled and/or expanded expandable member with the blood vessel portion in contact creates a sealing thus obstructing and/or diminishing substantially a fluid passing therebetween.

In different exemplary embodiments, a valving mechanism may include an additional valve or a seal for sealing around a guide wire passing therethrough, and/or selectively seal an opening or a segment of an infusion lumen when the guide wire is removed or otherwise absent. In some embodiments, a catheter includes at least one one-way valve allowing a guide wire passing therethough while sealing fluid passage. Optionally, the one-way valve is disposed adjacent to catheter's distal end and/or between a distal opening and a lateral infusion opening in the infusion lumen. Optionally, alternatively or additionally, the one-way valve is disposed adjacent to catheter's proximal end and/or between a proximal opening and a lateral infusion opening in the infusion lumen. Optionally, the catheter and/or the valving mechanism includes a septum seal.

Figure 2A:
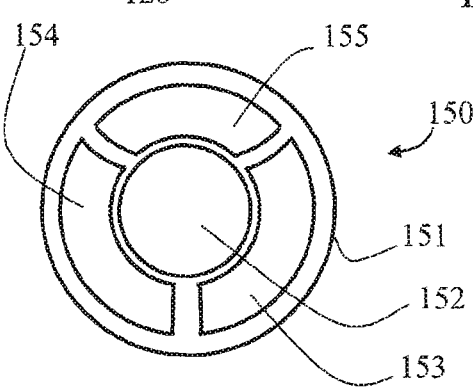
FIGS. 2A-2E schematically illustrate cut and side views of different balloon catheters designs having separate infusion and inflation lumens, in accordance with some embodiments of the present invention.
Figure 2B:
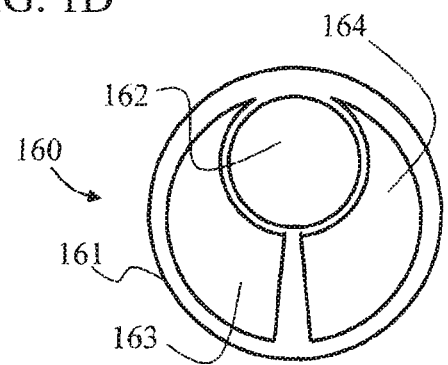

FIGS. 2A-2E schematically illustrate cut and side views of different balloon catheters designs having separate infusion and inflation lumens, in accordance with embodiments of the present invention. FIG. 2A shows a cross section in a shaft 151 of a dilatation-infusion balloon catheter 150 which includes four separate lumens sealed one to the other: a guidewire lumen 152, a balloon inflation lumen 153, a contrast enhancing media delivery lumen 154, and a drug delivery lumen 155. FIG. 2B shows a cross section in a shaft 161 of a dilatation-infusion balloon catheter 160 which includes three separate lumens sealed one to the other: a guidewire lumen 162, a balloon inflation lumen 163, and an infusion lumen 164 capable of delivering contrast enhancing media and/or medicament.

In some embodiments, a dilatation catheter according to present exemplary disclosures comprises a plurality of adjacent fluid exits comprising and/or included as part of a fluid exit. The fluid exits are arranged radially and/or longitudinally. The fluid exit(s) includes an opening. Optionally, additionally or alternatively, the fluid exit(s) includes normally closed lips, such as in a slit design.

In some embodiments, a dilatation catheter with an expandable member includes at a distal end thereof a plurality of openings in direct communication with an infusion lumen. In some embodiments, the plurality of openings comprises at least one distal opening distal to the expandable member and at least one proximal opening proximal to the expandable member. In some embodiments, the plurality of openings are configured such that a ratio between a first exit flow rate, through the at least one distal opening, and a second exit flow rate, through the at least one proximal opening, can be regulated or met in relation to a known pressure gradient therebetween. Optionally, the plurality of openings is configured such that the total cross section of the at least one distal opening is smaller than the total cross section of the at least one proximal opening by a known derivative. Optionally, the known derivative is equal or greater than 1.2, optionally equal or greater than 1.5, optionally equal or greater than 2, optionally equal or greater than 5, optionally equal or greater than 10, optionally equal or greater than 100, or higher, or lower, or an intermediate value. Optionally, alternatively or additionally, the regulation is determined by guidewire positioning in the infusion lumen.

Figure 2C:
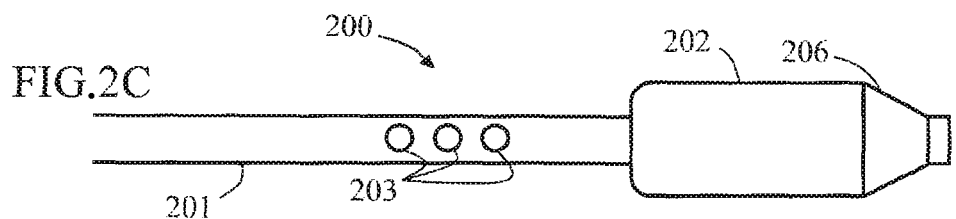
Figure 2D:
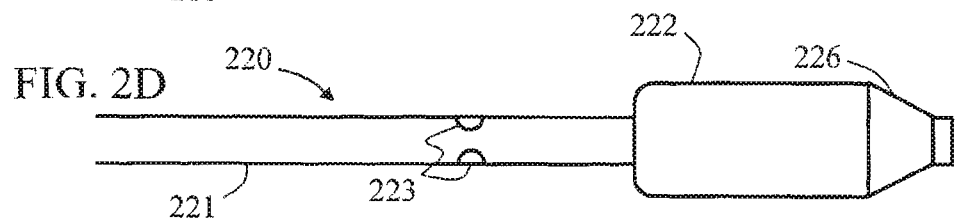
Figure 2E:
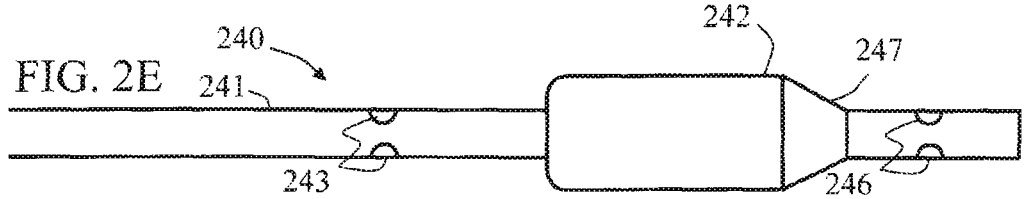

FIG. 2C shows a partial side view of a dilatation-infusion balloon catheter 200 that comprises a shaft 201, a balloon 202 and a beveled tip 206, both disposed at distal end of shaft 201. Shaft 201 houses a plurality of lumens (not shown); one is an infusion lumen with a fluid exit comprising longitudinally staggered openings 203. FIG. 2D shows a partial side view of a dilatation-infusion balloon catheter 220 that comprises a shaft 221, a balloon 222 and a beveled tip 226, both disposed at distal end of shaft 221. Shaft 221 houses a plurality of lumens (not shown); one is an infusion lumen with a fluid exit comprising circularly staggered openings 223. FIG. 2E shows a partial side view of a dilatation-infusion balloon catheter 240 that comprises a shaft 241, a balloon 242 and a beveled tip 247, both disposed at distal end of shaft 241. Shaft 241 houses a plurality of lumens (not shown); one is an infusion lumen with a fluid exit comprising proximal openings 243 and distal openings 246, whereas balloon 242 is disposed therebetween.

Exemplary Embodiments of Rapid Exchange (RX) Infusion Catheters

In some embodiments, exemplary catheters of the present invention are based upon rapid exchange (RX) platform having a substantially shorter over-the-wire length than a standard over-the-wire (OTW) platform based catheter. Rapid exchange balloon angioplasty is a standard of care in many interventional procedures and enables ease of use and comfort to the operator. In several instances when a combination of drug infusion and angioplasty with a RX balloon is needed, the procedure is more difficult and may necessitate removal of the balloon catheter and exchanging it with a different catheter then injecting the medication and then replacing the balloon over the wire if needed.

In some embodiments, an RX balloon catheter of the present invention includes a fluid outlet, optionally distal and/or proximal to a dilatation balloon. In some embodiments, a fluid outlet in an RX balloon catheter of the present invention is not intended also to serve as a guidewire opening. In some embodiments, a fluid outlet, proximal and/or distal to the dilatation balloon, is located adjacent the balloon, while the distance between the two guidewire openings is 10 to 30 centimeters, optionally 20 to 25 centimeters, to allow comfortable handling by the operator. In some embodiments, means are provided to prevent guidewire exit through a fluid outlet and/or that fluid does not escape or infiltrate through a guidewire opening.

Reference is made to FIGS. 3A-3C which schematically illustrate an exemplary rapid exchange balloon catheter 250, in accordance with embodiments of the present invention. In some embodiments, balloon catheter 250 comprises a shaft 251 that includes an infusion wall 252 and an inflation wall 253. Infusion wall 252 encloses an infusion lumen 254 extending axially therealong and comprises a fluid inlet 256 and a fluid outlet 257 located distally to fluid inlet 256. Inflation wall 253 encloses an inflation lumen 255 extending axially therealong opened at a distal end thereof into an inner volume of a dilatation balloon 258. Fluid outlet 257 includes a single opening (although it may include a plurality of openings) located proximally to balloon 258, optionally distanced 1 cm or less from proximal boundary 268 of balloon 258.

In some embodiments, and as shown in FIG. 3A, infusion wall 252 does not extend distally up to proximal boundary 268 and/or is not connected to balloon 258, so that fluid outlet 257 can be located at a distal surface opposing the balloon (as shown). Optionally and alternatively, infusion wall 252 extends up to proximal boundary 268 and/or is connected to balloon 258 (not shown) so that a different location for a fluid outlet is needed, optionally laterally to the shaft 251 at infusion wall 252, adjacent proximal boundary 268.

In some embodiments, there may be a need to provide means in the infusion lumen to allow correct delivery of a guidewire through the proximal guidewire opening while "bypassing" the fluid outlet which is located between the proximal guidewire opening and the distal guidewire opening. In some embodiments, balloon catheter 250 includes a guidewire channel 259. Guidewire channel 259 optionally includes a tubular section, and may be sealed or unsealed to infusion lumen 254 and to inflation lumen 255. Guidewire channel 259 is sized to closely fit, snugly, over a prescribed guidewire 260 for allowing unhindered passing therethrough with guidewire 260. A prescribed guidewire may include any size and length of guidewire, including but not limited to 0.035" (inch), 0.025", 0.018", and/or 0.014" guidewires. In some embodiments, guidewire channel 259 comprises a channel distal end 261 protruding distally from balloon 258 with a distal guidewire opening 262, and a channel proximal end 263 with a proximal guidewire opening 264 at shaft 251 between fluid inlet 256 and fluid outlet 257.

Guidewire channel 259 includes an inclined portion 265 configured to skew guidewire 260 upon forcing it therethrough. In some embodiments, inclined portion 265 is curved towards inflation wall 253 and infusion wall 252, and passes through a hole 267 at inflation wall 253 while proximal guidewire opening 264 is provided through a hole 266 at infusion wall 252. In some embodiments, proximal guidewire opening 264 is distanced 10 cm to 30 cm from distal guidewire opening 262 therefore allowing the usability of the RX platform.

In some embodiments, at least one of infusion wall 252 and inflation wall 253 includes a hypotube and/or a different form of rigid tube-like element as a portion thereof. A hypotube member or portion can serve to add rigidity to shaft 251, especially proximally to proximal guidewire opening 264. In some embodiments, shaft 251, one or both of infusion wall 252 and inflation wall 253, is segmented and includes segments of different forms and/or rigidity. In some such embodiments, infusion lumen 252 includes a rigid segment (e.g., hypotube) proximally to proximal guidewire opening 264 while an underlapping portion of inflation wall 253 is substantially less rigid and optionally flexible and/or elastic. Optionally and alternatively, infusion lumen 252 includes a flexible segment proximally to proximal guidewire opening 264 while an overlapping portion of inflation wall 253 is substantially rigid (e.g., hypotube).

FIGS. 4A-4C schematically illustrate an exemplary rapid exchange balloon catheter 270, in accordance with embodiments of the present invention. Unlike balloon catheter 250 which includes concentric distribution of the lumens (i.e., a first lumen-enclosing wall provided inside a second lumen-enclosing wall), balloon catheter 270 includes a multiple-lumen type shaft, in this example double-lumen (i.e., the lumens are divided in a single encompassing wall and/or are extruded together to form a shaft). In some embodiments, balloon catheter 270 comprises a shaft 271 that includes an infusion wall 272 and an inflation wall 273. Infusion wall 272 encloses an infusion lumen 274 extending axially therealong and comprises a fluid inlet 276 and a fluid outlet 277 located distally to fluid inlet 276. Inflation wall 273 encloses an inflation lumen 275 extending axially therealong opened at a distal end thereof into an inner volume of a dilatation balloon 278. Fluid outlet 277 includes a single opening (although it may include a plurality of openings) located proximally to balloon 278, optionally distanced 1 cm or less from proximal boundary 288 of balloon 258.

In some embodiments, balloon catheter 270 includes a guidewire channel 279. Guidewire channel 279 optionally includes a tubular section, and may be sealed or unsealed to infusion lumen 274 and to inflation lumen 275. Guidewire channel 279 is sized to closely fit, snugly, over a prescribed guidewire 280 for allowing unhindered passing therethrough with guidewire 280. A prescribed guidewire may include any size and length of guidewire, including but not limited to 0.035" (inch), 0.025", 0.018", and/or 0.014" guidewires. In some embodiments, guidewire channel 279 comprises a channel distal end 281 protruding distally from balloon 278 with a distal guidewire opening 282, and a channel proximal end 283 with a proximal guidewire opening 284 at shaft 271 between fluid inlet 276 and fluid outlet 277.

Guidewire channel 279 includes an inclined portion 285 configured to skew guidewire 280 upon forcing it therethrough. Inclined portion 285 is curved towards infusion wall 272 and proximal guidewire opening 284 is provided through a hole 286 at infusion wall 272. In some embodiments, proximal guidewire opening 284 is distanced 10 cm to 30 cm from distal guidewire opening 282 therefore allowing the usability of the RX platform.

FIGS. 5A-5C schematically illustrate an exemplary rapid exchange balloon catheter 270', in accordance with embodiments of the present invention. Unlike balloon catheter 270 which includes a single opening proximal to the dilatation balloon, balloon catheter 270' includes an opening distal to the balloon as well. In some embodiments, balloon catheter 270' comprises a shaft 271' that includes an infusion wall 272' and an inflation wall 273'. Infusion wall 272' encloses an infusion lumen 274' extending axially therealong and comprises a fluid inlet 276' and a fluid outlet 277' located distally to fluid inlet 276'. Inflation wall 273' encloses an inflation lumen 275' extending axially therealong opened at a distal end thereof into an inner volume of a dilatation balloon 278'. Fluid outlet 277' includes a single proximal opening 289' (or alternatively a plurality of openings) located proximally to balloon 278', optionally distanced 1 cm or less from a proximal boundary 288' of balloon 258', as well as a single distal opening 290' (or alternatively a plurality of openings) located distally to balloon 278'.

In some embodiments, balloon catheter 270' includes a guidewire channel 279'. Guidewire channel 279' optionally includes a tubular section, and may be sealed or unsealed to infusion lumen 274' and to inflation lumen 275'. Guidewire channel 279' is sized to closely fit, snugly, over a prescribed guidewire 280' for allowing unhindered passing therethrough with guidewire 280'. A prescribed guidewire may include any size and length of guidewire, including but not limited to 0.035" (inch), 0.025", 0.018", and/or 0.014" guidewires. In some embodiments, guidewire channel 279' comprises a channel distal end 281' protruding distally from balloon 278' with a distal guidewire opening 282', and a channel proximal end 283' with a proximal guidewire opening 284' at shaft 271' between fluid inlet 276' and fluid outlet 277'.

Guidewire channel 279' includes an inclined portion 285' configured to skew guidewire 280' upon forcing it therethrough. Inclined portion 285' is curved towards infusion wall 272' and proximal guidewire opening 284' is provided through a hole 286' at infusion wall 272'. In some embodiments, proximal guidewire opening 284' is distanced 10 cm to 30 cm from distal guidewire opening 282' therefore allowing the usability of the RX platform.

Applications and Exemplary Embodiments of Methods for Imaging and Treating a Blood Vessel An aspect of some embodiments of the present invention relates to methods for treating a blood vessel using exemplary catheters comprising both dilatation means and infusion means. Optionally, the infusion means are provided proximally to the dilatation means. The exemplary catheters may include an over-the-wire platform or a rapid-exchange platform for catheter delivery.

FIGS. 6A-6F schematically illustrate possible scenarios in a method for imaging and treating a blood vessel AR using an exemplary balloon catheter 290, in accordance with embodiments of the present invention. Balloon catheter 290 includes a shaft 291, a dilatation balloon 292 provided at the distal end of shaft 291, and a plurality of openings provided on the shaft including a fluid inlet 293, a fluid outlet 294 adjacent dilatation balloon 292, a distal guidewire opening 295, and a proximal guide opening 296 located between fluid outlet 294 and fluid inlet 293. Optionally, fluid outlet 294 is located proximally to dilatation balloon 292. In some embodiments, balloon catheter 290 is an RX type catheter and in some such embodiments, a distance L is met between proximal guidewire opening 296 and a proximal boundary 297 of dilatation balloon 292. Distance L is optionally 50 centimeters (cm) or less, optionally 30 cm or less, optionally 20 cm or less, optionally 10 cm or less, optionally 5 cm or less, or higher, or lower, or an intermediate distance.

In some embodiments, the method may include preliminary steps for locating a lesion LS in blood vessel AR, assessing its condition and choosing balloon size and other catheter and/or treatment parameters. Blood vessel may be an obstructed coronary artery or a vasospatic cerebral blood vessel. At first a percutaneous access is created using an introducer needle and/or a sheath introducer (not shown). A guiding catheter is passed (not shown) through the introducer sheath and pushed forward until reaching blood vessel AR before lesion LS. Contrast enhancing medium may then be injected (not shown) via the guiding catheter into blood vessel AR and real-time imaging can be used.

As shown in FIG. 6A, a guidewire GW is inserted in blood vessel AR and provided across lesion LS. As shown in FIG. 6B, guidewire GW is passed through distal guidewire opening 295 and proximal guidewire opening 296 in balloon catheter 290, and the latter is then pushed in blood vessel AR such that fluid outlet 294 is in approximation with lesion LS (as shown in FIG. 6C).

As shown in FIG. 6D, a contrast enhancing medium CM in injected from fluid outlet 294. In some embodiments, the total amount of contrast medium CM used (optionally in one episode or in all episodes of the treatment) is equal or less than 5 cc for producing an angiogram of lesion LS and surroundings, optionally 2 cc or less, optionally 1 cc or less, or higher, or lower, or intermediate.

Medicament can then be delivered to the lesion (not shown). Any medicament may be used, including but not limited to thrombolytic agent and/or vasodilator agent (e.g., nicardipine or nifedipine). The medicament can be delivered from fluid outlet 294. Optionally, fluid inlet 293 and/or fluid outlet 294 is flushed with a cleaning medium (e.g., saline) between contrast medium CM injections and medicament deliveries.

In some embodiments, and as shown in FIG. 6E, dilatation balloon 292 can be expanded to dilate blood vessel AR about lesion LS. Balloon expansion can be performed before medicament delivering and/or before contrast medium injecting. Optionally, alternatively or additionally, Balloon expansion can be performed after medicament delivering and/or after contrast medium injecting. Optionally, contrast medium injecting is repeated after medicament delivering and/or after balloon expanding.

When needed, dilatation balloon 292 can be deflated (as shown in FIG. 6F). In some embodiments, contrast medium injecting is repeated after balloon deflating. Medication delivery can be performed before and/or after balloon deflation.

Optionally (not shown), dilatation balloon is provided enclosed with a collapsed expandable member, such as a stent. Such an expandable member may be self-expandable or balloon-expandable.

Reference is now made to FIGS. 7A-7F which schematically illustrate possible scenarios in a method for revascularizing a blood vessel AR using a dilatation catheter 330, in accordance with embodiments of the present invention. The target portion in blood vessel AR includes a stenotic region ST further obstructed with thrombus or embolus, such as blood clots BC, diminishing or preventing a blood flow BF therethrough. In some embodiments, blood vessel AR is a coronary artery in a condition of myocardial infarction, optionally in acute state.

In some embodiments, the method includes preliminary steps for reaching the target portion in blood vessel AR, for assessing its condition and for choosing balloon size and other catheter and/or treatment parameters. At first a percutaneous access is created, optionally in the femoral artery, using an introducer needle and/or a sheath introducer (not shown). A guiding catheter 310 is passed through the introducer sheath and pushed forward until reaching the entry of blood vessel AR. Contrast enhancing medium is injected via guiding catheter 310 into blood vessel AR and real-time imaging is used for locating the target portion in blood vessel AR filled with the obstruction. A guidewire 320 is then inserted through the lumen of guiding catheter 310 into blood vessel AR, passing across the entire length and beyond the target portion, as shown in FIG. 7A. Dilatation catheter 330 can then be passed over guidewire 320 towards the target portion. Optionally, dilatation catheter 330 is pushed in blood vessel AR in the direction of blood flow BF.

Dilatation catheter 330 comprises an elongated tubular wall 331 enclosing an infusion lumen (not shown) extending between a proximal end and a distal end thereof, an expandable member 332, and a fluid exit 334, located at wall 331 proximally to expandable member 332, in fluid communication with the infusion lumen. As shown in FIG. 7B, dilatation catheter 330 is positioned in blood vessel AR such that expandable member 332 is in apposition to the target portion and fluid exit 334 is toward the obstructing blood clots BC (relative to blood flow BF direction). In some embodiments, expandable member 332 is made from a non-compliant or a semi-compliant material useful for dilatations, optionally under medium to high inflation pressures.

Optionally and alternatively, expandable member 332 is made from a compliant material. Catheter 330 includes a guidewire opening 333 at its distal end through which guidewire 320 can pass unhindered. Optionally, guidewire opening 333 is opened to the infusion lumen. In some such embodiments, guidewire 320 may serve as an obstructing member in a valving mechanism to prevent or diminish infusion lumen to pass through guidewire opening 333, allowing it to exit only/mainly from fluid outlet 334.

An optional preliminary step prior to dilatation, shown in FIG. 7C, includes injecting an obstruction treatment fluid DR through the infusion lumen via fluid exit 334 until a chosen amount is accumulated above the obstructing clots BC. Optionally the obstruction treatment fluid DR includes a thrombolytic agent, such as a tissue plasminogen activator (e.g., tPA). The accumulated amount may be at least 1 cc, optionally at least 2 cc, optionally at least 5 cc, or higher, or lower, or an intermediate volume. Optionally, the obstructing clots BC is allowed to soak in the accumulated treatment fluid DR for a chosen period, optionally between seconds to minutes, optionally at least 5 seconds, optionally at least 30 seconds, optionally at least 2 minutes, optionally at least 5 minutes, or higher, or lower, or an intermediate time period.

As shown in FIG. 7D, expandable member 332 is expanded to dilate blood vessel AR about the target portion. This way blood clots BC and optional plaque is crushed outwardly and stenosis ST is pressed open. Expandable member 332 may be kept expanded as needed, either continuously or in repetitions. As shown in FIG. 7E, expandable member 332 can serve for occluding about the target portion for allowing soaking of remaining and/or entrapped blood clots BC in an accumulated treatment fluid DR for a chosen period of time, injected via fluid outlet 334, similarly to as described above. As shown in FIG. 7F, expandable member 332 is then deflated to collapse during and/or after which, optionally, treatment fluid DR is further poured through fluid outlet 334 merging with the restored blood flow BF flowing distally in the artery. Afterwards catheter 330 is removed and the medical intervention is completed.

Optionally, a contrast enhancing medium is delivered via catheter 330 adjacent the obstructing blood clots BC between expandable member 332 and fluid exit 334, optionally through the infusion lumen and fluid exit 334. Optionally and alternatively, contrast enhancing medium is delivered through a second lumen (not shown) sealed to the infusion lumen. Contrast media delivery may occur continuously or repeatedly before, during and/or after expanding and/or collapsing of expandable member 332. In case infusion lumen is used to deliver different fluid types therethrough, such as contrast enhancing medium and treatment fluid DR, the infusion lumen may optionally be flushed, optionally with saline, between fluids injecting/delivering.

Reference is made to FIGS. 8A-8C which schematically illustrate possible scenarios in a method for revascularizing a blood vessel using a dilatation catheter 430, in accordance with embodiments of the present invention. Dilatation catheter 430 comprises an elongated tubular wall 431 enclosing an infusion lumen (not shown) extending between a proximal end and a distal end thereof, an expandable member 432, and a fluid exit 434, located at wall 431 proximally to expandable member 432, in fluid communication with the infusion lumen. In some embodiments, expandable member 432 is made from a non-compliant or a semi-compliant material useful for dilatations, optionally under medium to high inflation pressures. Optionally and alternatively, expandable member 432 is made from a compliant material. Catheter 430 includes a guidewire opening 433 at its distal end through which a guidewire 420 can pass unhindered. Guidewire opening 433 is opened to the infusion lumen and guidewire 420 may serve as an obstructing member in a valving mechanism to prevent or diminish infusion lumen to pass through guidewire opening 433, allowing it to exit only/mainly from fluid outlet 434.

The preliminary steps described above may be performed in this example in full or in part. FIG. 8A shows dilatation catheter 430 positioned in blood vessel AR such that expandable member 432 is in apposition to the target portion and fluid exit 434 is toward the obstructing blood clots BC (relative to blood flow BF direction). As shown in FIG. 8B, expandable member 432 is expanded to dilate blood vessel AR about the target portion. This way blood clots BC and optional plaque is crushed outwardly and stenosis ST is pressed open. Expandable member 432 may be kept expanded as needed, either continuously or in repetitions.

Expandable member 432 can serve for occluding about the target portion for allowing soaking of remaining and/or entrapped blood clots BC in an accumulated treatment fluid DR for a chosen period of time, injected via fluid outlet 434. Optionally the obstruction treatment fluid DR includes a thrombolytic agent, such as a tissue plasminogen activator (e.g., tPA). The accumulated amount may be at least 1 cc, optionally at least 2 cc, optionally at least 5 cc, or higher, or lower, or an intermediate volume. Optionally, the obstructing clots BC is allowed to soak in the accumulated treatment fluid DR for a chosen period, optionally between seconds to minutes, optionally at least 5 seconds, optionally at least 30 seconds, optionally at least 2 minutes, optionally at least 5 minutes, or higher, or lower, or an intermediate time period.

Besides possibly soaking blood clots BC with the accumulated treatment fluid, treatment fluid DR may be delivered beyond the target portion and expandable member 432 through guidewire opening 433. For facilitating such distal fluid delivery, guidewire 420 is withdrawn partly, optionally proximally to fluid exit 434 or optionally to a position between fluid exit 434 and guidewire opening 433.

As shown in FIG. 8C, expandable member 432 is then deflated to collapse during and/or after which, optionally, treatment fluid DR is further poured through fluid outlet 434 and/or guidewire opening 433 merging with the restored blood flow BF flowing distally in the artery. Afterwards catheter 430 is removed and the medical intervention is completed.

Optionally, a contrast enhancing medium is delivered via catheter 430 adjacent the obstructing blood clots BC between expandable member 432 and fluid exit 434, optionally through the infusion lumen and fluid exit 434. Optionally and alternatively, contrast enhancing medium is delivered also through guidewire opening 433. Optionally and alternatively, contrast enhancing medium is delivered through a second lumen (not shown) sealed to the infusion lumen. Contrast media delivery may occur continuously or repeatedly before, during and/or after expanding and/or collapsing of expandable member 432. In case infusion lumen is used to deliver different fluid types therethrough, such as contrast enhancing medium and treatment fluid DR, the infusion lumen may optionally be flushed, optionally with saline, between fluids injecting/delivering.

Figure 9C:
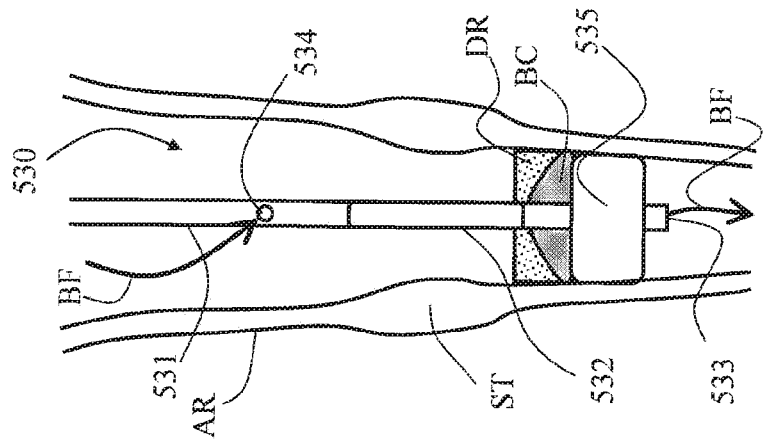
FIGS. 9A-9C schematically illustrate possible scenarios in a method for revascularizing a blood vessel using a third exemplary dilatation catheter, in accordance with some embodiments of the present invention.
Figure 9B:
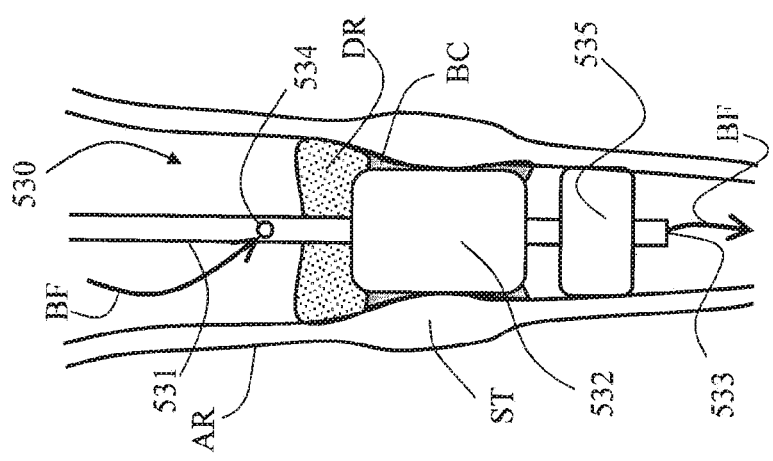
Figure 9A:
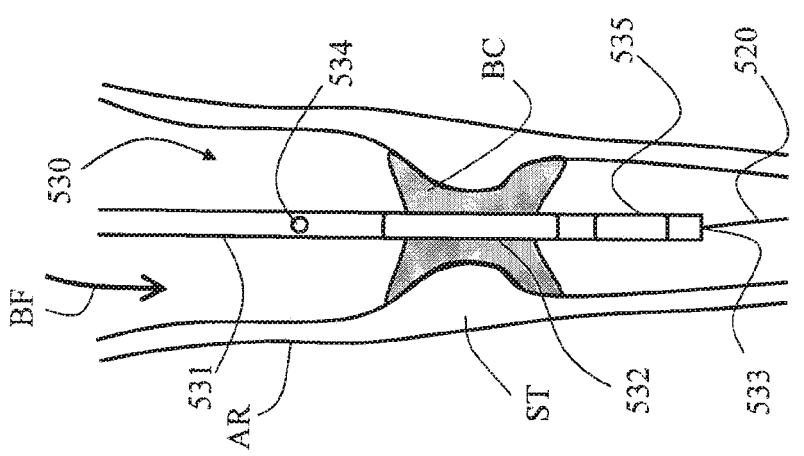

Reference is made to FIGS. 9A-9C which schematically illustrate possible scenarios in a method for revascularizing a blood vessel using a dilatation catheter 530, in accordance with embodiments of the present invention. Dilatation catheter 530 comprises an elongated tubular wall 531 enclosing an infusion lumen (not shown) extending between a proximal end and a distal end thereof, an expandable dilatation member 532, an expandable occlusion member 535 located distally to dilatation member 532, and a fluid exit 534, located at wall 531 proximally to dilatation member 532, in fluid communication with the infusion lumen. In some embodiments, dilatation member 532 is made from a non-compliant or a semi-compliant material useful for dilatations, optionally under medium to high inflation pressures. Occlusion member 535 is made from a compliant material capable of conforming at expansion to boundaries of enclosing blood vessel portion thereby facilitating sealing to fluid passage therebetween. Optionally though not necessarily dilatation balloon 532 and occlusion balloon 535 communicate with separate inflation lumens (not shown), so that each inflation or deflation is independent with the other. Catheter 530 includes a guidewire opening 533 at its distal end through which a guidewire 520 can pass unhindered. Guidewire opening 533 is opened to the infusion lumen and guidewire 520 may serve as an obstructing member in a valving mechanism to prevent or diminish infusion lumen to pass through guidewire opening 533, allowing it to exit only/mainly from fluid outlet 534.

The preliminary steps described above may be performed in this example in full or in part. FIG. 9A shows dilatation catheter 530 positioned in blood vessel AR such that dilatation member 532 is in apposition to the target portion and fluid exit 534 is toward the obstructing blood clots BC (relative to blood flow BF direction). As shown in FIG. 9B, dilatation member 532 is expanded to dilate blood vessel AR about the target portion. This way blood clots BC and optional plaque is crushed outwardly and stenosis ST is pressed open. Dilatation member 532 may be kept expanded as needed, either continuously or in repetitions.

Occlusion member 535 may also be expanded for occluding a portion of blood vessel AR beyond/distal to the target portion the target portion for allowing soaking of remaining and/or entrapped blood clots BC in an accumulated treatment fluid DR for a chosen period of time, injected via fluid outlet 534 (as in the example shown in FIG. 9C). Optionally the obstruction treatment fluid DR includes a thrombolytic agent, such as a tissue plasminogen activator (e.g., tPA). The accumulated amount may be at least 1 cc, optionally at least 2 cc, optionally at least 5 cc, or higher, or lower, or an intermediate volume. Optionally, the obstructing clots BC is allowed to soak in the accumulated treatment fluid DR for a chosen period, optionally between seconds to minutes, optionally at least 5 seconds, optionally at least 30 seconds, optionally at least 2 minutes, optionally at least 5 minutes, or higher, or lower, or an intermediate time period.

Besides possibly soaking blood clots BC with the accumulated treatment fluid, treatment fluid DR may be delivered beyond occlusion member 535 through guidewire opening 533. For facilitating such distal fluid delivery, guidewire 520 is withdrawn partly, optionally proximally to fluid exit 534 or optionally to a position between fluid exit 534 and guidewire opening 533.

In some embodiments, catheter 530 may allow blood perfusion therethrough by allowing blood BF flowing in blood vessel AR to insert a first infusion opening at a first location proximal to dilatation member 532 and/or occlusion member 535 and exit a second infusion opening at a second location distal to occlusion member 535. In some embodiments, in case an infusion lumen serves also for guidewire passing, as shown in FIGS. 9A-9C, guidewire 520 can be withdrawn proximally to fluid exit 534 for facilitating blood perfusion between fluid exit 534 and guidewire opening 533.

At final stages of the treatment, dilatation member 532 and occlusion member 535 are deflated to collapse during and/or after which, optionally, treatment fluid DR may further be poured through fluid outlet 534 and/or guidewire opening 533 merging with the restored blood flow BF flowing distally in the artery. Afterwards catheter 530 can be removed and the medical intervention is completed.

Optionally, a contrast enhancing medium is delivered via catheter 530 adjacent the obstructing blood clots BC between dilatation member 532 and fluid exit 534, optionally through the infusion lumen and fluid exit 534. Optionally and alternatively, contrast enhancing medium is delivered also through guidewire opening 533. Optionally and alternatively, contrast enhancing medium is delivered through a second lumen (not shown) sealed to the infusion lumen. Contrast media delivery may occur continuously or repeatedly before, during and/or after expanding and/or collapsing of dilatation member 532 and/or occlusion member 535. In case infusion lumen is used to deliver different fluid types therethrough, such as contrast enhancing medium and treatment fluid DR, the infusion lumen may optionally be flushed, optionally with saline, between fluids injecting/delivering.

Figure 10A:
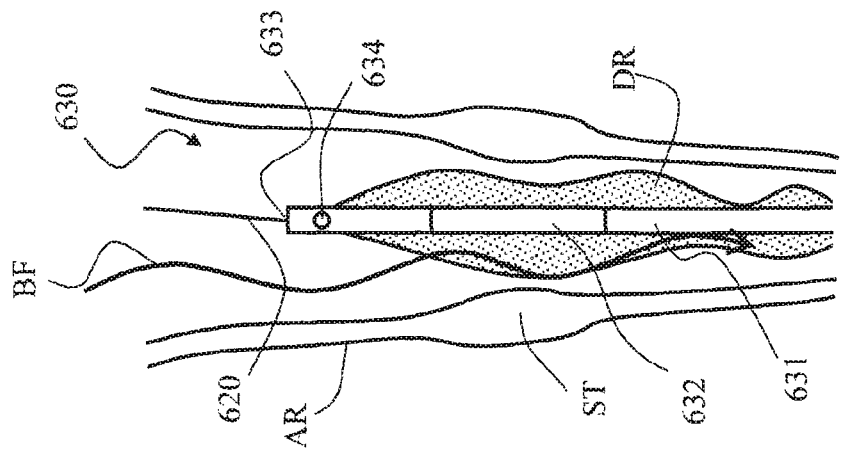
FIGS. 10A-10C schematically illustrate possible scenarios in a method for revascularizing a blood vessel using a fourth exemplary dilatation catheter, in accordance with some embodiments of the present invention.
Figure 10B:
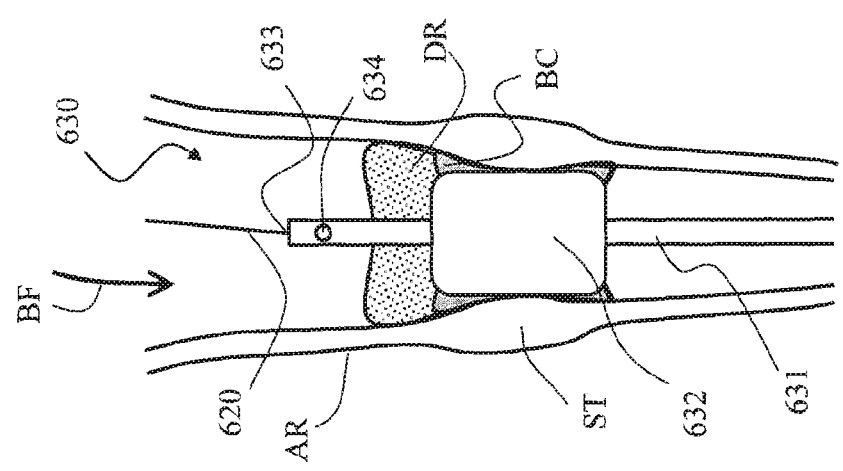
Figure 10C:
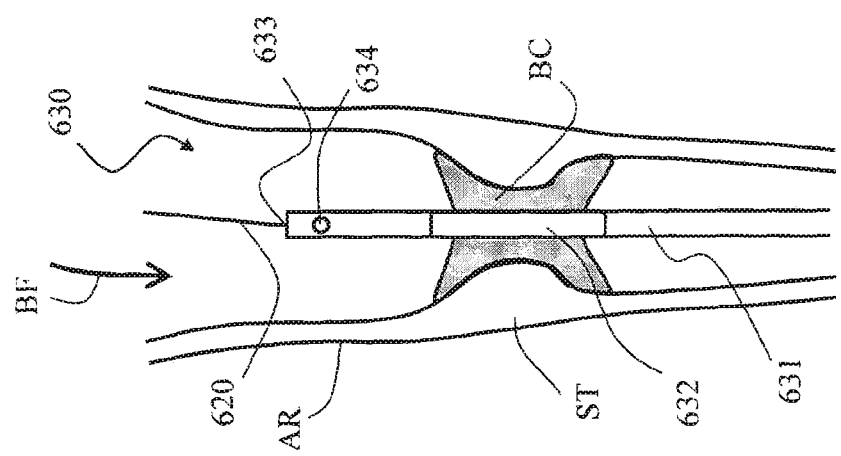

FIGS. 10A-10C schematically illustrate possible scenarios in a method for revascularizing a blood vessel using a dilatation catheter 630, in accordance with embodiments of the present invention. In this embodiment, catheter 630 is passed in blood vessel AR in opposite direction to blood floe BF direction. Dilatation catheter 630 comprises an elongated tubular wall 631 enclosing an infusion lumen (not shown) extending between a proximal end and a distal end thereof, an expandable member 632, and a fluid exit 634, located at wall 631 distally to expandable member 632, in fluid communication with the infusion lumen. In some embodiments, expandable member 632 is made from a non-compliant or a semi-compliant material useful for dilatations, optionally under medium to high inflation pressures. Optionally and alternatively, expandable member 632 is made from a compliant material. Catheter 630 includes a guidewire opening 633 at its distal end through which a guidewire 620 can pass unhindered.

The preliminary steps described above may be performed in this example in full or in part. FIG. 10A shows dilatation catheter 630 positioned in blood vessel AR such that expandable member 632 is in apposition to the target portion and fluid exit 634 is toward the obstructing blood clots BC (relative to blood flow BF direction). As shown in FIG. 10B, expandable member 632 is expanded to dilate blood vessel AR about the target portion. This way blood clots BC and optional plaque is crushed outwardly and stenosis ST is pressed open. Expandable member 632 may be kept expanded as needed, either continuously or in repetitions.

Expandable member 632 can serve for occluding about the target portion for allowing soaking of remaining and/or entrapped blood clots BC in an accumulated treatment fluid DR for a chosen period of time, injected via fluid outlet 634. Optionally the obstruction treatment fluid DR includes a thrombolytic agent, such as a tissue plasminogen activator (e.g., tPA). The accumulated amount may be at least 1 cc, optionally at least 2 cc, optionally at least 5 cc, or higher, or lower, or an intermediate volume. Optionally, the obstructing clots BC is allowed to soak in the accumulated treatment fluid DR for a chosen period, optionally between seconds to minutes, optionally at least 5 seconds, optionally at least 30 seconds, optionally at least 2 minutes, optionally at least 5 minutes, or higher, or lower, or an intermediate time period. As shown in FIG. 10C, expandable member 632 is then deflated to collapse during and/or after which, optionally, treatment fluid DR is further poured through fluid outlet 634 merging with the restored blood flow BF flowing distally in the artery. Afterwards catheter 630 is removed and the medical intervention is completed.

Optionally, a contrast enhancing medium is delivered via catheter 630 adjacent the obstructing blood clots BC between expandable member 632 and fluid exit 634, optionally through the infusion lumen and fluid exit 634. Optionally and alternatively, contrast enhancing medium is delivered through a second lumen (not shown) sealed to the infusion lumen. Contrast media delivery may occur continuously or repeatedly before, during and/or after expanding and/or collapsing of expandable member 632. In case infusion lumen is used to deliver different fluid types therethrough, such as contrast enhancing medium and treatment fluid DR, the infusion lumen may optionally be flushed, optionally with saline, between fluids injecting/delivering.

FIGS. 11A-11C schematically illustrate possible scenarios in a method for revascularizing a blood vessel using a dilatation catheter 730 carrying a stent 735, in accordance with embodiments of the present invention. Dilatation catheter 730 comprises an elongated tubular wall 731 enclosing an infusion lumen (not shown) extending between a proximal end and a distal end thereof, an expandable member 732, and a fluid exit 734, located at wall 731 proximally to expandable member 732, in fluid communication with the infusion lumen. In some embodiments, expandable member 732 is made from a non-compliant or a semi-compliant material useful for dilatations, optionally under medium to high inflation pressures. Optionally and alternatively, expandable member 732 is made from a compliant material. Catheter 730 includes a guidewire opening 733 at its distal end through which a guidewire 720 can pass unhindered. Guidewire opening 733 is opened to the infusion lumen and guidewire 720 may serve as an obstructing member in a valving mechanism to prevent or diminish infusion lumen to pass through guidewire opening 733, allowing it to exit only/mainly from fluid outlet 734.

Stent 735 may be any mechanical intraluminal artifact for supporting a vessel wall in a chosen lumen diameter. Stent 735 may be made from polymer or metal, self-expandable or balloon-expandable, woven, laser cut or etched, or otherwise designed and manufactured.

The preliminary steps described above may be performed in this example in full or in part. FIG. 11A shows dilatation catheter 730 positioned in blood vessel AR such that expandable member 732 is in apposition to the target portion and fluid exit 734 is toward the obstructing blood clots BC (relative to blood flow BF direction). As shown in FIG. 11B, expandable member 732 is expanded to dilate blood vessel AR about the target portion. This way blood clots BC and optional plaque is crushed outwardly and stenosis ST is pressed open. Stent 735 is also expanded by expansion of expandable member 732 for permanent fixation in the target portion. Expandable member 732 may be kept expanded as needed, either continuously or in repetitions.

Expandable member 732 can serve for occluding about the target portion for allowing soaking of remaining and/or entrapped blood clots BC in an accumulated treatment fluid DR for a chosen period of time, injected via fluid outlet 734. Optionally the obstruction treatment fluid DR includes a thrombolytic agent, such as a tissue plasminogen activator (e.g., tPA). The accumulated amount may be at least 1 cc, optionally at least 2 cc, optionally at least 5 cc, or higher, or lower, or an intermediate volume. Optionally, the obstructing clots BC is allowed to soak in the accumulated treatment fluid DR for a chosen period, optionally between seconds to minutes, optionally at least 5 seconds, optionally at least 30 seconds, optionally at least 2 minutes, optionally at least 5 minutes, or higher, or lower, or an intermediate time period.

Besides possibly soaking blood clots BC with the accumulated treatment fluid, treatment fluid DR may be delivered beyond the target portion and expandable member 732 through guidewire opening 733. For facilitating such distal fluid delivery, guidewire 720 may be withdrawn partly, optionally proximally to fluid exit 734 or optionally to a position between fluid exit 734 and guidewire opening 733.

As shown in FIG. 11C, expandable member 732 is then deflated to collapse during and/or after which, optionally, treatment fluid DR is further poured through fluid outlet 734 and/or guidewire opening 733 merging with the restored blood flow BF flowing distally in the artery. Stent 735 is shown still in its permanently expanded form fixed to wall of target portion in blood vessel AR. Afterwards catheter 730 is removed and the medical intervention is completed.

Optionally, a contrast enhancing medium is delivered via catheter 730 adjacent the obstructing blood clots BC between expandable member 732 and fluid exit 734, optionally through the infusion lumen and fluid exit 734. Optionally and alternatively, contrast enhancing medium is delivered also through guidewire opening 733. Optionally and alternatively, contrast enhancing medium is delivered through a second lumen (not shown) sealed to the infusion lumen. Contrast media delivery may occur continuously or repeatedly before, during and/or after expanding and/or collapsing of expandable member 732. In case infusion lumen is used to deliver different fluid types therethrough, such as contrast enhancing medium and treatment fluid DR, the infusion lumen may optionally be flushed, optionally with saline, between fluids injecting/delivering.

Applications and Exemplary Embodiments of Treating an Aortic Stenosis

Reference is now made to FIGS. 12A-12E which schematically illustrate possible scenarios in a method for treating an aortic stenosis, in accordance with embodiments of the present invention. The method can be performed using a dilatation catheter 800 which comprises an elongated tubular wall 810 enclosing an infusion lumen (not shown), an expandable member 820 located at a distal end of wall 810, and a fluid exit 840 at wall 810 being in fluid communication with the lumen. Expandable member 820 is provided contracted and enclosed with a collapsed expandable valve prosthesis 830, which may be self-expandable or balloon-expandable.

Figure 12A:
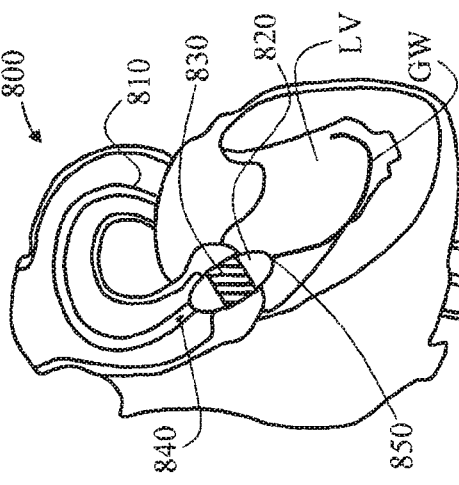
FIGS. 12A-12E schematically illustrate possible scenarios in a method for treating an aortic stenosis, in accordance with some embodiments of the present invention.

As shown in FIG. 12A, a guidewire GW is inserted through an Aorta into the left ventricle LV of a Heart, against blood flow BF direction.

Figure 12B:
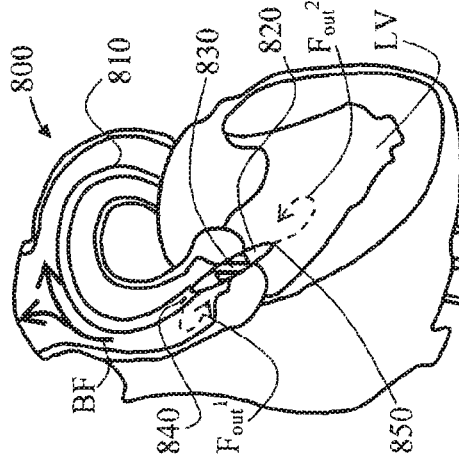

As shown in FIG. 12B, dilatation catheter 800 is passed over guidewire GW such that expandable member 820 is in apposition to a native aortic valve AoV. Optionally, a contrast enhancing medium can be delivered (shown as $F_{out}^1$) adjacent natural aortic valve AoV between expandable member 820 and fluid exit 840. Contrast enhancing medium is optionally delivered through the infusion lumen and fluid exit 840. Optionally and alternatively, the contrast enhancing medium is delivered through a second lumen sealed to the infusion lumen.

Optionally, contrast medium can also be delivered via a distal guidewire opening 850 (shown as $F_{out}^1$) at distal end of dilatation catheter 800, into left ventricle LV, optionally when guidewire GW is withdrawn and do not obstruct it.

Figure 12C:
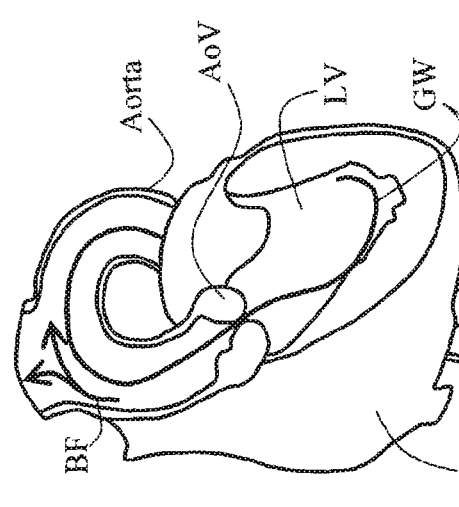

Expandable member 820 can then be expanded to dilate aortic valve AoV, as shown in FIG. 12C in parallel to occluding the entrance to aortic valve AoV. Contrast medium delivery can occur continuously or repeatedly before, during and/or after expandable member expansion.

Figure 12D:
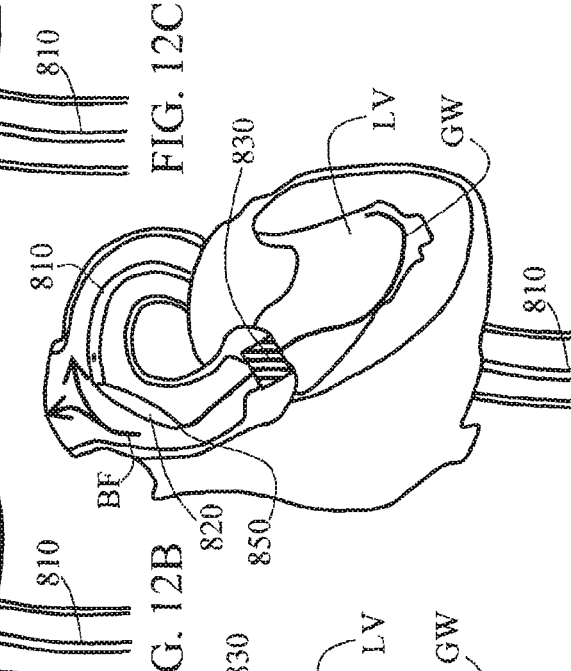
Figure 12E:
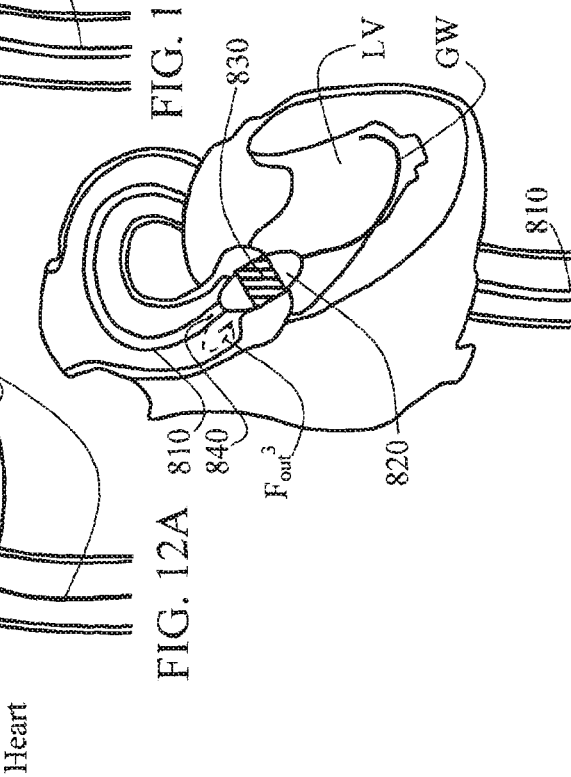

As shown in FIG. 12D, a fluid $F_{out}^3$ may be injected through the infusion lumen via fluid exit 840. Fluid $F_{out}^3$ can be a medicament. Fluid $F_{out}^3$ may be injected before, during and/or after balloon expanding. The infusion lumen can flushed with cleaning medium (e.g., saline) between different fluid injections such as between medicament injecting and contrast medium delivering.

In some embodiments, expandable member 820 is repeatedly expanded and contracted in a timely manner for allowing blood flowing from left ventricle LV to the Aorta in between medicament injection and/or contrast enhancing medium delivery.

When needed, expandable member 820 may be contracted and dilatation catheter 800 may be removed, leaving behind the deployed occlusion member 830. Contrast medium delivery can occur continuously or repeatedly before, during and/or after expandable member contraction. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for imaging and treating a blood vessel, the method comprising:
   inserting a guidewire in a blood vessel having a lesion such that the guidewire is provided across the lesion;
   providing a balloon catheter comprising:
      a shaft including:
         an infusion wall, wherein the infusion wall and an outer surface of the shaft define an infusion lumen; and
         an inflation wall defining an inflation lumen;
      a dilatation balloon coupled to said shaft, the dilation balloon defining a proximal boundary;
      a fluid inlet in fluid communication with the infusion lumen, the fluid outlet adjacent said dilatation balloon, wherein a distal end of the infusion wall is disposed proximally of the proximal boundary thereby defining a fluid outlet is disposed at the distal end of the infusion wall opposing the balloon; and
      a guidewire channel fluidly isolated from the infusion lumen and the inflation lumen, the guidewire channel having a distal guidewire opening, and a proximal guidewire opening defined in the shaft and located between said fluid outlet and said fluid inlet and distanced 30 cm or less from the proximal boundary of said dilatation balloon, wherein said guidewire channel includes an inclined portion disposed within said shaft and configured to skew said guidewire upon forcing thereof through said inclined portion, the inclined portion extending through at least one of the inflation wall or the infusion wall;
   passing said guidewire through said distal guidewire opening and said proximal guidewire opening and pushing said balloon catheter in the blood vessel such that said fluid outlet is in approximation with the lesion;
   injecting a contrast enhancing medium from said fluid outlet in a total amount equal or less than 2 cc and producing an angiogram of the lesion; and
   delivering medicament to the lesion.

2. A method according to claim 1, wherein said total amount is equal or less than 1 cc of contrast enhancing medium.

3. A method according to claim 1, wherein said medicament is delivered from said fluid outlet.

4. A method according to claim 3, wherein at least one of the fluid inlet or the fluid outlet is flushed with a cleaning medium between said injecting and said delivering.

5. A method according to claim 1, wherein said medicament includes a thrombolytic agent.

6. A method according to claim 1, wherein said blood vessel is an obstructed coronary artery.

7. A method according to claim 1, further comprising:
expanding said dilatation balloon to dilate the blood vessel about the lesion.

8. A method according to claim 7, wherein said expanding is performed before said delivering.

9. A method according to claim 7, wherein said expanding is performed before said injecting.

10. A method according to claim 7, wherein said expanding is performed after said delivering.

11. A method according to claim 1, wherein said injecting is repeated after said delivering.

12. A method according to claim 7, wherein said injecting is repeated after said expanding.

13. A method according to claim 7, further comprising: deflating said dilatation balloon.

14. A method according to claim 13, wherein said injecting is repeated after said deflating.

15. A method according to claim 13, wherein said delivering is performed after said deflating.

16. A method according to claim 13, wherein said delivering is performed before said deflating.

17. A method according to claim 7, wherein said dilatation balloon is provided enclosed with a collapsed expandable member such as a stent.

18. A method according to claim 17, wherein said expandable member is self-expandable.

19. A method according to claim 17, wherein said expandable member is balloon-expandable.

20. A method according to claim 1, wherein said fluid outlet is located proximally to said dilatation balloon.

21. A method according to claim 1, wherein said inclined portion extends transversely through said inflation wall and said infusion wall.

* * * * *